US011136560B2

(12) United States Patent
Hibi et al.

(10) Patent No.: US 11,136,560 B2
(45) Date of Patent: Oct. 5, 2021

(54) PIPECOLINIC ACID 4-HYDROXYLASE AND METHOD FOR PRODUCING 4-HYDROXY AMINO ACID USING SAME

(71) Applicant: API CORPORATION, Tokyo (JP)

(72) Inventors: Makoto Hibi, Kyoto (JP); Jun Ogawa, Kyoto (JP); Ryoma Miyake, Kanagawa (JP); Hiroshi Kawabata, Kanagawa (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 15/947,220

(22) Filed: Apr. 6, 2018

(65) Prior Publication Data

US 2018/0282709 A1    Oct. 4, 2018

Related U.S. Application Data

(62) Division of application No. 15/115,028, filed as application No. PCT/JP2015/052126 on Jan. 27, 2015, now Pat. No. 9,969,988.

(30) Foreign Application Priority Data

Jan. 31, 2014   (JP) ................. 2014-017716

(51) Int. Cl.
  *C12N 9/02* (2006.01)
  *C12N 1/20* (2006.01)
  (Continued)

(52) U.S. Cl.
  CPC ............ *C12N 9/0071* (2013.01); *C12N 1/20* (2013.01); *C12P 13/04* (2013.01); *C12P 17/10* (2013.01);
  (Continued)

(58) Field of Classification Search
  None
  See application file for complete search history.

(56) References Cited

U.S. PATENT DOCUMENTS

| 5,508,272 A | 4/1996 | Roble |
| 2002/0137146 A1* | 9/2002 | Choi ................. C07K 14/53 |
| | | 435/69.7 |

(Continued)

FOREIGN PATENT DOCUMENTS

| JP | 7-48259 | 2/1995 |
| JP | 2009-526813 | 7/2009 |

(Continued)

OTHER PUBLICATIONS

UniProt Accession No. L2G7W2_COLGN, published Mar. 6, 2013 (Year: 2013).*

(Continued)

*Primary Examiner* — Richard C Ekstrom
(74) *Attorney, Agent, or Firm* — Greenblum & Bernstein, P.L.C.

(57) ABSTRACT

The present invention provides a pipecolic acid 4-hydroxylase protein exemplified by the following (A), (B), and (C), having activity to react with L-pipecolic acid in the presence of 2-oxoglutaric acid and iron(II) ions to produce trans-4-hydroxy-L-pipecolic acid, and a method for producing 4-hydroxy amino acid, which method comprises reacting the pipecolic acid 4-hydroxylase protein, cells containing the protein, a treated product of the cells, and/or a culture liquid obtained by culturing the cells, with α-amino acid to produce 4-hydroxy amino acid:

(A) a polypeptide comprising the amino acid sequence represented by SEQ ID NO:2, 4, 6, 8, 10, 12, 16, or 18;
(B) a polypeptide comprising the amino acid sequence represented by SEQ ID NO:2, 4, 6, 8, 10, 12, 16, or 18

(Continued)

except that one or several amino acids are deleted, substituted, and/or added, and having pipecolic acid 4-hydroxylase activity; and (C) a polypeptide having an amino acid sequence that is not less than 80% identical to the amino acid sequence represented by SEQ ID NO:2, 4, 6, 8, 10, 12, 16, or 18, and having pipecolic acid 4-hydroxylase activity.

3 Claims, 9 Drawing Sheets

Specification includes a Sequence Listing.

(51) Int. Cl.
  *C12P 13/04* (2006.01)
  *C12P 17/12* (2006.01)
  *C12P 17/10* (2006.01)
(52) U.S. Cl.
  CPC ............. *C12P 17/12* (2013.01); *C12Y 114/00* (2013.01); *C12Y 114/11006* (2013.01); *H05K 999/99* (2013.01)

(56) References Cited

U.S. PATENT DOCUMENTS

| | | | |
|---|---|---|---|
| 2009/0048231 | A1 | 2/2009 | Priepke et al. |
| 2010/0056566 | A1 | 3/2010 | Plettenburg et al. |
| 2015/0118719 | A1 | 4/2015 | Chen et al. |
| 2015/0211035 | A1 | 7/2015 | Fujii et al. |

FOREIGN PATENT DOCUMENTS

| | | |
|---|---|---|
| JP | 2010-514720 | 5/2010 |
| WO | 2013/134625 | 9/2013 |

OTHER PUBLICATIONS

UniProt Accession No. F9FPA3_FUSOF, published Oct. 19, 2011 (Year: 2011).*
UniProt Accession No. I8TNQ0_ASPO3, published Oct. 3, 2012 (Year: 2012).*
UniProt Accession No. B6H092_PENRW, published Dec. 16, 2008 (Year: 2008).*
UniProt Accession No. I1RHG1_GIBZE, published Jun. 13, 2012 (Year: 2012).*
UniProt Accession No. Q5BAP0_EMENI, published Apr. 26, 2005 (Year: 2005).*
UniProt Accession No. E6V835_VARPE, published Mar. 8, 2011 (Year: 2011).*
Gen Bank Accession No. EKJ73839.1, published Oct. 5, 2012 (Year: 2012).*
UniProt Accession No. K3VI07_FUSPC, published Nov. 28, 2012 (Year: 2012).*
UniProt Accession No. T0KZT2_COLGC, published Oct. 16, 2013 (Year: 2013).*
Shibasaki et al., "Microbial Poline 4-Hydroxylase Screening and Gene Cloning," *Appl. Environ. Microbiol.*, vol. 65, No. 9, pp. 4028-4031, Sep. 1999.
Hibi et al., "Characterization of *Bacillus thuringiensis* L-Isoleucine Dioxygenase for Production of Useful Amino Acids," *Appl. and Environ. Microbiol.*, vol. 77, No. 19, pp. 6926-6930, Oct. 2011.
Klein et al., "A Simple Prodecure for Selective Hydroxylation of L-Proline and L-Pipecolic Acid with Recombinantly Expressed Proline Hydroxylases," *Adv. Synth. Catal.*, vol. 353, Issue 8, pp. 1375-1383, May 2011.
Occhiato et al., "A Short and Convenient Synthesis of Enantiopure cis- and trans-4-Hydroxypipecolic Acid," *Synthesis*, No. 21, pp. 3611-3616, 2009.
Bork et al., "Icatibant," *Nature Reviews Drug Discovery*, vol. 7, pp. 801-802, Oct. 2008.
Hopkins et al., "SCY-635, a Novel Nonimmunosuppressive Analog of Cyclosporine That Exhibits Potent Inhibition of Hepatitis C Virus RNA Replication In Vitro," *Antimicrobial Agents and Chemotherapy*, vol. 54, No. 2, pp. 660-672, Feb. 2010.
Cordero et al., "The Synthesis of 4-Hydroxypipecolic Acids by Stereoselective Cycloaddition of Configurationally Stable Nitrones," *Eur. J. of Org. Chem.*, vol. 2006, Issue 14, pp. 3235-3241, Jul. 2006.
Kimura et al., "A New Synthetic Method for the Preparation of α, β-Didehydroamino Acid Derivatives by Means of a Wittig-Type Reaction. Syntheses of (2S, 4S)- and (2R, 4R)-4-Hydroxyprolines," *Bull. Chem. Soc. Jpn.*, vol. 75, No. 11, pp. 2517-2525, Nov. 2002.
Gardiner et al., Database GenBank, Accession No. EGU81245, "hypothetical protein FOXB_08233 [Fusarium oxysporum Fo5176]," <http://www.ncbi.nlm.nih.gov/protein/EGU81245.1>, Aug. 5, 2011, [retrieved on Mar. 16, 2015].
Zhao et al., Database GenBank Accession No. EIT75558, "iron/ascorbate family oxidoreductase [Aspergillus oryzae 3.042]," <http://www.ncbi.nlm.nih.gov/protein/EIT75558.1>, Jun. 18, 2012, [retrieved on Mar. 16, 2015].
Kiel et al., Database GenBank Accession No. CAP80999, "Pc12g13720 [Penicillium rubens Wisconsin 54/1255]", <http://www.ncbi.nlm.nih.gov/protein/CAP80999.1>, Aug. 21, 2013, [retrieved on Mar. 16, 2015].
Birren et al., Database GenBank Acecession No. ESU10046, "hypothetical protein FGSG_03213 [Fusarium gramineamm PH-1]," http://www.ncbi.nlm.nih.gov/protein/ESU10046.1, Nov. 22, 2013, [retrieved on Mar. 16, 2015].
Gan et al., Database Genbank Accession No. ELA34460, "thymine dioxygenase [Colletotrichum gloeosporioides Nara gc5," <http://www.ncbi.nlm.nih.gov/protein/ELA34460.1>, Dec. 14, 2012, [retrieved on Mar. 16, 2015].
Brown et al., Database GenBank Accession No. EJL74608, "hypothetical protein PMI12_03076 [*Variovorax* sp. CF313]," <http://www.ncbi.nlm.nih.gov/protein/EJL74608.1>, Jul. 27, 2012, [retrieved on Mar. 16, 2015].
Galagan et al., Database GenBank, Accession No. EAA64501, "hypothetical protein AN2390.2 [Aspergillus nidulans FGSC A4]," <http://www.ncbi.nlm.nih.gov/protein/EAA64501.1>, Sep. 9, 2004, [retrieved on Mar. 16, 2015].
International Search Report issued in Patent Application No. PCT/JP2015/052126, dated Mar. 31, 2015.
International Preliminary Report on Patentability issued in Patent Application No. PCT/JP2015/052126, dated Aug. 11, 2016.
Molnár et al., "Validation of high-affinity binding sites for succinic acid through distinguishable binding of gamma-hydroxybutyric acid receptor-specific NCS 382 antipodes," Bioorganic & Medicinal Chemistry Letters, 18, pp. 6290-6292 (2008).
European Extended Search Report for European Application No. 15742961.4 dated May 29, 2017.
Office Action issued in EP 15 742 961.4 dated Feb. 5, 2019.
Japanese Office Action dated Feb. 19, 2019 in corresponding Japanese Application No. 2015-559939 with machine English-language translation.
Li Chen et al., "Genomics-driven discovery of the pneumocandin biosynthetic gene cluster in the fungus Glarea lozoyensis," BMC Genomics, 2013, vol. 14, No. 339, pp. 1-18.
Clavaminate synthase-like protein [Glarea lozoyensis ATCC 20868], GenBank, accession No. EPE34347.1 published Jun. 14, 2013, (retrieved from https://www.ncbi.nih.gov/protein/epe34347.1?report=girevhist.).
L. Petersen et al., "Novel proline hydroxylase activities in pneumocandin-producing fungus Glarea lozoyensis responsible for the formation of trans 3- and trans 4-hydroxyproline," Appl. Microbiol. Biotechnol., 2003, vol. 62, pp. 263-267.
Makoto Hibi, "Development of amino acid oxygenases useful as asymmetric conversion catalysts," The 14th Enzyme Application Symposium, Research Encouragement Price Winner Lecture, Subject 3. Nagoya, Japan on Jun. 14, 2013, Amano Enzyme Inc.

(56) References Cited

OTHER PUBLICATIONS

Zheng You et al., "Pentalenolacetone biosynthesis, molecular cloning and assignment of biochemical function to Pt1H, a non-heme iron dioxygenase of Streptomyces avermitilis," J. Am. Chem. Soc., 2006, vol. 128, pp. 6566-6567.

Chinese Office Action dated Feb. 22, 2019 in Chinese Patent Application No. 201580006796.4 and English-language translation thereof.

Decision of Rejection issued in JP Patent Application No. 2015-559939, dated Dec. 10, 2019, along with a machine English-language translation.

Smirnov et al., "A Novel Family of Bacterial Dioxygenases that Catalyse the Hydroxylation of Free L-Amino Acids", *FEMS Microbiol. Lett.*, vol. 331, pp. 97-104 (2012).

L-isoleucine-4-hydroxylase [Bacillus thuringiensis], GenBank/GenPept, Accession No. ADJ94127.1, (Sep. 21, 2010), [retrieved Mar. 26, 2021].

Hypothetical protein Varpa_4217 [Variovorax paradoxus EPS], GenBank/GenPept, Accession No. YP_004156498, (Jun. 10, 2013), [retrieved Mar. 26, 2021].

Variovorax paradoxus EPS, complete genome, GenBank/GenPept, Accession No. CP002417, (Dec. 31, 2013), [retrieved Mar. 26, 2021].

Office Action issued in JP Patent Application No. 2020-041237, dated Apr. 6, 2021, along with an English language translation.

\* cited by examiner

SEQUENCE LISTING

<160> NUMBER OF SEQ ID NOS: 18

<210> SEQ ID NO 1
<211> LENGTH: 1014
<212> TYPE: DNA
<213> ORGANISM: Fusarium oxysporum c8D
<220> FEATURE:
<221> NAME/KEY: CDS
<222> LOCATION: (1)..(1014)

<400> SEQUENCE: 1

| | | | | | | | | | | | | | | | | |
|---|---|---|---|---|---|---|---|---|---|---|---|---|---|---|---|---|
| atg | gcc | gcc | ctc | aac | gca | gac | acc | ctc | gac | atg | tcc | ctc | ttc | ttc | ggc | 48 |
| Met | Ala | Ala | Leu | Asn | Ala | Asp | Thr | Leu | Asp | Met | Ser | Leu | Phe | Phe | Gly | |
| 1 | | | | 5 | | | | | 10 | | | | | 15 | | |

| acc | ccc | tcc | cag | aag | caa | gac | ttc | tgc | gac | tcc | ctc | ctg | cgc | ctg | ctc | 96 |
|---|---|---|---|---|---|---|---|---|---|---|---|---|---|---|---|---|
| Thr | Pro | Ser | Gln | Lys | Gln | Asp | Phe | Cys | Asp | Ser | Leu | Leu | Arg | Leu | Leu | |
| | | | 20 | | | | | 25 | | | | | 30 | | | |

| aaa | aag | cgc | ggg | ggc | gtc | aag | ctg | atc | aac | cac | ccc | atc | ccc | tcc | acc | 144 |
|---|---|---|---|---|---|---|---|---|---|---|---|---|---|---|---|---|
| Lys | Lys | Arg | Gly | Gly | Val | Lys | Leu | Ile | Asn | His | Pro | Ile | Pro | Ser | Thr | |
| | | 35 | | | | | 40 | | | | | 45 | | | | |

| tcc | atc | cac | gag | ctc | ttc | gca | cag | aca | aag | cgc | ttc | ttc | aac | ctc | ccc | 192 |
|---|---|---|---|---|---|---|---|---|---|---|---|---|---|---|---|---|
| Ser | Ile | His | Glu | Leu | Phe | Ala | Gln | Thr | Lys | Arg | Phe | Phe | Asn | Leu | Pro | |
| | 50 | | | | | 55 | | | | | 60 | | | | | |

| ctc | gag | aca | aaa | atg | ctc | gcc | aag | cac | cct | ccc | cag | gca | aac | ccg | aac | 240 |
|---|---|---|---|---|---|---|---|---|---|---|---|---|---|---|---|---|
| Leu | Glu | Thr | Lys | Met | Leu | Ala | Lys | His | Pro | Pro | Gln | Ala | Asn | Pro | Asn | |
| 65 | | | | | 70 | | | | | 75 | | | | | 80 | |

| cgc | ggg | tac | tcc | ttc | gtc | ggc | cag | gaa | aac | gtc | gcc | aac | atc | agt | ggt | 288 |
|---|---|---|---|---|---|---|---|---|---|---|---|---|---|---|---|---|
| Arg | Gly | Tyr | Ser | Phe | Val | Gly | Gln | Glu | Asn | Val | Ala | Asn | Ile | Ser | Gly | |
| | | | | 85 | | | | | 90 | | | | | 95 | | |

| tac | gaa | aag | ggt | ctt | gga | ccg | cta | aag | act | cgt | gac | atc | aag | gag | act | 336 |
|---|---|---|---|---|---|---|---|---|---|---|---|---|---|---|---|---|
| Tyr | Glu | Lys | Gly | Leu | Gly | Pro | Leu | Lys | Thr | Arg | Asp | Ile | Lys | Glu | Thr | |
| | | | 100 | | | | | 105 | | | | | 110 | | | |

| gtg | gac | ttt | gga | tcg | gcg | aat | gat | gag | ctt | gtt | gat | aac | ctt | tgg | gtt | 384 |
|---|---|---|---|---|---|---|---|---|---|---|---|---|---|---|---|---|
| Val | Asp | Phe | Gly | Ser | Ala | Asn | Asp | Glu | Leu | Val | Asp | Asn | Leu | Trp | Val | |
| | | 115 | | | | | 120 | | | | | 125 | | | | |

| ccg | gag | gag | gag | ttg | ccc | ggt | ttt | agg | agc | ttt | atg | gag | ggg | ttt | tat | 432 |
|---|---|---|---|---|---|---|---|---|---|---|---|---|---|---|---|---|
| Pro | Glu | Glu | Glu | Leu | Pro | Gly | Phe | Arg | Ser | Phe | Met | Glu | Gly | Phe | Tyr | |
| | 130 | | | | | 135 | | | | | 140 | | | | | |

| gag | ttg | gct | ttc | aag | acg | gag | atg | cag | ctt | ctt | gag | gct | ctt | gct | att | 480 |
|---|---|---|---|---|---|---|---|---|---|---|---|---|---|---|---|---|
| Glu | Leu | Ala | Phe | Lys | Thr | Glu | Met | Gln | Leu | Leu | Glu | Ala | Leu | Ala | Ile | |
| 145 | | | | | 150 | | | | | 155 | | | | | 160 | |

| gct | ctt | ggt | gtt | tct | ccc | gat | cac | ttg | aag | tcg | ctg | cat | aac | cgt | gct | 528 |
|---|---|---|---|---|---|---|---|---|---|---|---|---|---|---|---|---|
| Ala | Leu | Gly | Val | Ser | Pro | Asp | His | Leu | Lys | Ser | Leu | His | Asn | Arg | Ala | |
| | | | | 165 | | | | | 170 | | | | | 175 | | |

| gag | aat | gag | ttt | cga | atc | ttg | cac | tac | ccc | gcc | att | cct | gcc | tca | gaa | 576 |
|---|---|---|---|---|---|---|---|---|---|---|---|---|---|---|---|---|
| Glu | Asn | Glu | Phe | Arg | Ile | Leu | His | Tyr | Pro | Ala | Ile | Pro | Ala | Ser | Glu | |
| | | | 180 | | | | | 185 | | | | | 190 | | | |

| ctc | gca | gac | ggt | aca | gca | acc | cgc | atc | gca | gag | cac | aca | gat | ttc | gga | 624 |
|---|---|---|---|---|---|---|---|---|---|---|---|---|---|---|---|---|
| Leu | Ala | Asp | Gly | Thr | Ala | Thr | Arg | Ile | Ala | Glu | His | Thr | Asp | Phe | Gly | |
| | | 195 | | | | | 200 | | | | | 205 | | | | |

| acc | atc | acc | atg | ctt | ttc | caa | gac | tct | gtc | ggt | ggc | ctt | cag | gtc | gag | 672 |
|---|---|---|---|---|---|---|---|---|---|---|---|---|---|---|---|---|
| Thr | Ile | Thr | Met | Leu | Phe | Gln | Asp | Ser | Val | Gly | Gly | Leu | Gln | Val | Glu | |
| | 210 | | | | | 215 | | | | | 220 | | | | | |

| gac | caa | gag | aac | ctc | gga | aca | ttc | aac | aac | gtc | gaa | tca | gct | tcc | ccc | 720 |
|---|---|---|---|---|---|---|---|---|---|---|---|---|---|---|---|---|
| Asp | Gln | Glu | Asn | Leu | Gly | Thr | Phe | Asn | Asn | Val | Glu | Ser | Ala | Ser | Pro | |
| 225 | | | | | 230 | | | | | 235 | | | | | 240 | |

| aca | gac | atc | atc | ctc | aac | atc | ggt | gat | tct | ctg | cag | agg | ttg | acg | aat | 768 |
|---|---|---|---|---|---|---|---|---|---|---|---|---|---|---|---|---|
| Thr | Asp | Ile | Ile | Leu | Asn | Ile | Gly | Asp | Ser | Leu | Gln | Arg | Leu | Thr | Asn | |
| | | | | 245 | | | | | 250 | | | | | 255 | | |

| gac | act | ttc | aag | gct | gcg | tgt | cat | cgc | gtt | aca | tac | cct | cct | tct | atc | 816 |
|---|---|---|---|---|---|---|---|---|---|---|---|---|---|---|---|---|
| Asp | Thr | Phe | Lys | Ala | Ala | Cys | His | Arg | Val | Thr | Tyr | Pro | Pro | Ser | Ile | |

-continued

```
aaa gct ggt gat ggc gag cag gtc att cct gag aga tac tct atc gct    864
Lys Ala Gly Asp Gly Glu Gln Val Ile Pro Glu Arg Tyr Ser Ile Ala
        275                 280                 285 tac ttt gct aag cct aac cga agc gct tcg ttg ttt ccg ctg aag gag    912
Tyr Phe Ala Lys Pro Asn Arg Ser Ala Ser Leu Phe Pro Leu Lys Glu
290                 295                 300 ttt att gag gag ggc gtt cct tgt aaa tat gag gat gta act gct tgg    960
Phe Ile Glu Glu Gly Val Pro Cys Lys Tyr Glu Asp Val Thr Ala Trp
305                 310                 315                 320 gag tgg aat aac cgc cgt att gag aag ttg ttt tct gct gaa gct aag   1008
Glu Trp Asn Asn Arg Arg Ile Glu Lys Leu Phe Ser Ala Glu Ala Lys
                325                 330                 335 gct taa                                                            1014
Ala
```

<210> SEQ ID NO 2
<211> LENGTH: 337
<212> TYPE: PRT
<213> ORGANISM: Fusarium oxysporum c8D

<400> SEQUENCE: 2

```
Met Ala Ala Leu Asn Ala Asp Thr Leu Asp Met Ser Leu Phe Phe Gly
1               5                   10                  15

Thr Pro Ser Gln Lys Gln Asp Phe Cys Asp Ser Leu Leu Arg Leu Leu
            20                  25                  30

Lys Lys Arg Gly Gly Val Lys Leu Ile Asn His Pro Ile Pro Ser Thr
        35                  40                  45

Ser Ile His Glu Leu Phe Ala Gln Thr Lys Arg Phe Phe Asn Leu Pro
    50                  55                  60

Leu Glu Thr Lys Met Leu Ala Lys His Pro Gln Ala Asn Pro Asn
65                  70                  75                  80

Arg Gly Tyr Ser Phe Val Gly Gln Glu Asn Val Ala Asn Ile Ser Gly
                85                  90                  95

Tyr Glu Lys Gly Leu Gly Pro Leu Lys Thr Arg Asp Ile Lys Glu Thr
            100                 105                 110

Val Asp Phe Gly Ser Ala Asn Asp Glu Leu Val Asp Asn Leu Trp Val
        115                 120                 125

Pro Glu Glu Leu Pro Gly Phe Arg Ser Phe Met Glu Gly Phe Tyr
    130                 135                 140

Glu Leu Ala Phe Lys Thr Glu Met Gln Leu Leu Glu Ala Leu Ala Ile
145                 150                 155                 160

Ala Leu Gly Val Ser Pro Asp His Leu Lys Ser Leu His Asn Arg Ala
                165                 170                 175

Glu Asn Glu Phe Arg Ile Leu His Tyr Pro Ala Ile Pro Ala Ser Glu
            180                 185                 190

Leu Ala Asp Gly Thr Ala Thr Arg Ile Ala Glu His Thr Asp Phe Gly
        195                 200                 205

Thr Ile Thr Met Leu Phe Gln Asp Ser Val Gly Gly Leu Gln Val Glu
    210                 215                 220

Asp Gln Glu Asn Leu Gly Thr Phe Asn Val Glu Ser Ala Ser Pro
225                 230                 235                 240

Thr Asp Ile Ile Leu Asn Ile Gly Asp Ser Leu Gln Arg Leu Thr Asn
                245                 250                 255

Asp Thr Phe Lys Ala Ala Cys His Arg Val Thr Tyr Pro Pro Ser Ile
            260                 265                 270
```

```
Lys Ala Gly Asp Gly Glu Gln Val Ile Pro Glu Arg Tyr Ser Ile Ala
            275                 280                 285

Tyr Phe Ala Lys Pro Asn Arg Ser Ala Ser Leu Phe Pro Leu Lys Glu
        290                 295                 300

Phe Ile Glu Glu Gly Val Pro Cys Lys Tyr Glu Asp Val Thr Ala Trp
305                 310                 315                 320

Glu Trp Asn Asn Arg Arg Ile Glu Lys Leu Phe Ser Ala Glu Ala Lys
                325                 330                 335

Ala

<210> SEQ ID NO 3
<211> LENGTH: 987
<212> TYPE: DNA
<213> ORGANISM: Aspergillus oryzae RIB40
<220> FEATURE:
<221> NAME/KEY: CDS
<222> LOCATION: (1)..(987)

<400> SEQUENCE: 3 atg agc gaa gca ctg gac ctg agc ctg ctg aag ggt acg cct gaa caa    48
Met Ser Glu Ala Leu Asp Leu Ser Leu Leu Lys Gly Thr Pro Glu Gln
1               5                   10                  15 cgt gag cag atc agc gcc gag ctg ttg cac gcg ttg aaa acc cgt ggt    96
Arg Glu Gln Ile Ser Ala Glu Leu Leu His Ala Leu Lys Thr Arg Gly
                20                  25                  30 ggc gtc aaa ctg aag aac cat ggt ctg ccg gat aag ctg gtg cac gag   144
Gly Val Lys Leu Lys Asn His Gly Leu Pro Asp Lys Leu Val His Glu
            35                  40                  45 ctg ttc gat tgg act cgc aag ttc ttt gct ctg ccg cat gag gac aag   192
Leu Phe Asp Trp Thr Arg Lys Phe Phe Ala Leu Pro His Glu Asp Lys
        50                  55                  60 atg ctg gca aag cat ccg ccg cag gcg aat ccg aat cgt ggc tat tgt   240
Met Leu Ala Lys His Pro Pro Gln Ala Asn Pro Asn Arg Gly Tyr Cys
65                  70                  75                  80 tac gtt ggt cag gag tcg atc tct agc att tcc ggt tat gaa aaa ggc   288
Tyr Val Gly Gln Glu Ser Ile Ser Ser Ile Ser Gly Tyr Glu Lys Gly
                85                  90                  95 tta ccg caa ggt cgc ttt gtg cgc gac att aag gaa acg gtg gac ttc   336
Leu Pro Gln Gly Arg Phe Val Arg Asp Ile Lys Glu Thr Val Asp Phe
                100                 105                 110 ggc agc cca cgc gac gaa ctg gtc gat aac att tgg gtt ccg gag gaa   384
Gly Ser Pro Arg Asp Glu Leu Val Asp Asn Ile Trp Val Pro Glu Glu
            115                 120                 125 aaa ctg ccg ggt ttt cgt aag ttt atc gag gat ttc tac gaa acg tgc   432
Lys Leu Pro Gly Phe Arg Lys Phe Ile Glu Asp Phe Tyr Glu Thr Cys
        130                 135                 140 ttt aaa ctc gaa ctg gag atc ctg gcc gcc ctg gcg cgt gca ctg ggc   480
Phe Lys Leu Glu Leu Glu Ile Leu Ala Ala Leu Ala Arg Ala Leu Gly
145                 150                 155                 160 gtg gat gaa gat cac atg gtg tcc ctg cac aac aaa gcg gaa aac gag   528
Val Asp Glu Asp His Met Val Ser Leu His Asn Lys Ala Glu Asn Glu
                165                 170                 175 ttt cgt att ctg cac tat ccg gaa gtt ccg gca agc gag ctg gcg gat   576
Phe Arg Ile Leu His Tyr Pro Glu Val Pro Ala Ser Glu Leu Ala Asp
                180                 185                 190 ggt acc gct acc cgt atc gcg gag cat acc gat ttc ggt agc att acc   624
Gly Thr Ala Thr Arg Ile Ala Glu His Thr Asp Phe Gly Ser Ile Thr
            195                 200                 205 atg ctg ttt cag gac agc gtt ggt ggt ttg caa gtc gag gac caa caa   672
```

```
Met Leu Phe Gln Asp Ser Val Gly Gly Leu Gln Val Glu Asp Gln Gln
        210                 215                 220 aat ccg ggc gtg ttt cgt ggc atc gag agc gcg gac aaa acc gag atc      720
Asn Pro Gly Val Phe Arg Gly Ile Glu Ser Ala Asp Lys Thr Glu Ile
225                 230                 235                 240 att ctg aat att ggt gat agc atg cag cgt ctg acc aac gac acg ttc      768
Ile Leu Asn Ile Gly Asp Ser Met Gln Arg Leu Thr Asn Asp Thr Phe
                    245                 250                 255 cgt gca gcg tgt cac cgt gtt acg tac ccg ccg agc gtc aaa gtt ggc      816
Arg Ala Ala Cys His Arg Val Thr Tyr Pro Pro Ser Val Lys Val Gly
                260                 265                 270 tct gaa gca gtc atc ccg gag cgc tat tcc atc gcc tac ttc gct aaa      864
Ser Glu Ala Val Ile Pro Glu Arg Tyr Ser Ile Ala Tyr Phe Ala Lys
            275                 280                 285 cct aac cgt agc gcg agc ttg ttt ccg ttc aaa gag ttc att acc cca      912
Pro Asn Arg Ser Ala Ser Leu Phe Pro Phe Lys Glu Phe Ile Thr Pro
        290                 295                 300 agc acc ccg tgc cgt tac gag gat atc aat gcg tgg gac ttc cag aat      960
Ser Thr Pro Cys Arg Tyr Glu Asp Ile Asn Ala Trp Asp Phe Gln Asn
305                 310                 315                 320 ctg cgc att agc cgc ctg ttc aag taa                                  987
Leu Arg Ile Ser Arg Leu Phe Lys
                    325

<210> SEQ ID NO 4
<211> LENGTH: 328
<212> TYPE: PRT
<213> ORGANISM: Aspergillus oryzae RIB40

<400> SEQUENCE: 4

Met Ser Glu Ala Leu Asp Leu Ser Leu Leu Lys Gly Thr Pro Glu Gln
1               5                   10                  15

Arg Glu Gln Ile Ser Ala Glu Leu Leu His Ala Leu Lys Thr Arg Gly
                20                  25                  30

Gly Val Lys Leu Lys Asn His Gly Leu Pro Asp Lys Leu Val His Glu
            35                  40                  45

Leu Phe Asp Trp Thr Arg Lys Phe Phe Ala Leu Pro His Glu Asp Lys
        50                  55                  60

Met Leu Ala Lys His Pro Pro Gln Ala Asn Pro Asn Arg Gly Tyr Cys
65                  70                  75                  80

Tyr Val Gly Gln Glu Ser Ile Ser Ser Ile Ser Gly Tyr Glu Lys Gly
                    85                  90                  95

Leu Pro Gln Gly Arg Phe Val Arg Asp Ile Lys Glu Thr Val Asp Phe
                100                 105                 110

Gly Ser Pro Arg Asp Glu Leu Val Asp Asn Ile Trp Val Pro Glu Glu
            115                 120                 125

Lys Leu Pro Gly Phe Arg Lys Phe Ile Glu Asp Phe Tyr Glu Thr Cys
        130                 135                 140

Phe Lys Leu Glu Leu Glu Ile Leu Ala Ala Leu Ala Arg Ala Leu Gly
145                 150                 155                 160

Val Asp Glu Asp His Met Val Ser Leu His Asn Lys Ala Glu Asn Glu
                165                 170                 175

Phe Arg Ile Leu His Tyr Pro Glu Val Pro Ala Ser Glu Leu Ala Asp
                180                 185                 190

Gly Thr Ala Thr Arg Ile Ala Glu His Thr Asp Phe Gly Ser Ile Thr
            195                 200                 205

Met Leu Phe Gln Asp Ser Val Gly Gly Leu Gln Val Glu Asp Gln Gln
```

```
                210                 215                 220
Asn Pro Gly Val Phe Arg Gly Ile Glu Ser Ala Asp Lys Thr Glu Ile
225                 230                 235                 240

Ile Leu Asn Ile Gly Asp Ser Met Gln Arg Leu Thr Asn Asp Thr Phe
                245                 250                 255

Arg Ala Ala Cys His Arg Val Thr Tyr Pro Pro Ser Val Lys Val Gly
                260                 265                 270

Ser Glu Ala Val Ile Pro Glu Arg Tyr Ser Ile Ala Tyr Phe Ala Lys
            275                 280                 285

Pro Asn Arg Ser Ala Ser Leu Phe Pro Phe Lys Glu Phe Ile Thr Pro
        290                 295                 300

Ser Thr Pro Cys Arg Tyr Glu Asp Ile Asn Ala Trp Asp Phe Gln Asn
305                 310                 315                 320

Leu Arg Ile Ser Arg Leu Phe Lys
                325

<210> SEQ ID NO 5
<211> LENGTH: 987
<212> TYPE: DNA
<213> ORGANISM: Penicillium chrysogenum Wisconsin 54-1255
<220> FEATURE:
<221> NAME/KEY: CDS
<222> LOCATION: (1)..(987)

<400> SEQUENCE: 5 atg agc caa gcc ctt gat ttg tct ctg ctg aaa ggt agc ccg gaa gaa        48
Met Ser Gln Ala Leu Asp Leu Ser Leu Leu Lys Gly Ser Pro Glu Glu
1               5                   10                  15 cgt gat gaa gtt tcc gca gcc ctg ctg gac acc ttg aaa acc cgt ggt        96
Arg Asp Glu Val Ser Ala Ala Leu Leu Asp Thr Leu Lys Thr Arg Gly
                20                  25                  30 gtt gcg aaa ctg aag aac cac ggt ctg ccg gag gat ctg att gcc gag       144
Val Ala Lys Leu Lys Asn His Gly Leu Pro Glu Asp Leu Ile Ala Glu
            35                  40                  45 atg ttc gat tac acg cgc cgt ttc ttc agc ttg tcc ctg gag gac aag       192
Met Phe Asp Tyr Thr Arg Arg Phe Phe Ser Leu Ser Leu Glu Asp Lys
        50                  55                  60 atg acg gcg aag cac ccg cca gag gcg aac ccg aac cgc ggc tat agc       240
Met Thr Ala Lys His Pro Pro Glu Ala Asn Pro Asn Arg Gly Tyr Ser
65                  70                  75                  80 tac gtt ggc cag gag agc gtg tct agc atc tca ggt tat gaa aag ggt       288
Tyr Val Gly Gln Glu Ser Val Ser Ser Ile Ser Gly Tyr Glu Lys Gly
                85                  90                  95 tta ccg caa ggt aag act atc cgt gac att aaa gaa acc ctg gac atg       336
Leu Pro Gln Gly Lys Thr Ile Arg Asp Ile Lys Glu Thr Leu Asp Met
                100                 105                 110 ggc agc ccg cac gac tcg ctg gtc gat aac att tgg gtg gca gaa gag       384
Gly Ser Pro His Asp Ser Leu Val Asp Asn Ile Trp Val Ala Glu Glu
            115                 120                 125 aag ctg ccg ggt ttt cgc aag ttc atg gaa gat ttc tac gag agc tgt       432
Lys Leu Pro Gly Phe Arg Lys Phe Met Glu Asp Phe Tyr Glu Ser Cys
        130                 135                 140 ttc aaa gtg gaa ctg gag att ctg gat gcc ctg gcg cag gcg ctg gaa       480
Phe Lys Val Glu Leu Glu Ile Leu Asp Ala Leu Ala Gln Ala Leu Glu
145                 150                 155                 160 atc agc gct cct gat ctg cgt ctg ttg cac aat aaa gcg gag aat gag       528
Ile Ser Ala Pro Asp Leu Arg Leu Leu His Asn Lys Ala Glu Asn Glu
                165                 170                 175 ttc cgc ctg ctg cat tac cct gct gtt ccg gct agc gca ctg gag gat       576
```

```
                Phe Arg Leu Leu His Tyr Pro Ala Val Pro Ala Ser Ala Leu Glu Asp
                                180                 185                 190 ggc acc gca acg cgt atc gcg gag cac acg gac ttt ggc acc att acc        624
Gly Thr Ala Thr Arg Ile Ala Glu His Thr Asp Phe Gly Thr Ile Thr
            195                 200                 205 atg ttg ttt cag gac agc acc ggc ggt ctg caa gtg gag gac caa acc        672
Met Leu Phe Gln Asp Ser Thr Gly Gly Leu Gln Val Glu Asp Gln Thr
210                 215                 220 aat ctg ggt acc ttt cat gac gtc gtt agc ggt ggc aaa agc gaa atc        720
Asn Leu Gly Thr Phe His Asp Val Val Ser Gly Gly Lys Ser Glu Ile
225                 230                 235                 240 att ctg aac atc ggc gat agc ctg cag cgt ctg acc aat gac acg ttc        768
Ile Leu Asn Ile Gly Asp Ser Leu Gln Arg Leu Thr Asn Asp Thr Phe
                245                 250                 255 atg gcg gcg tgc cat cgt gtt acg tat ccg ccg acc gtc aaa gtg ggt        816
Met Ala Ala Cys His Arg Val Thr Tyr Pro Pro Thr Val Lys Val Gly
            260                 265                 270 tct gac gtc gtg att ccg gag cgc tac tcc gtc gcc tat ttt gcg aag        864
Ser Asp Val Val Ile Pro Glu Arg Tyr Ser Val Ala Tyr Phe Ala Lys
        275                 280                 285 ccg aat cgt atc gcg agc ctg ttt ccg ctg aaa aag ttt atc acc cca        912
Pro Asn Arg Ile Ala Ser Leu Phe Pro Leu Lys Lys Phe Ile Thr Pro
290                 295                 300 gca acg ccg tgc aag tat gaa gat att act gca tgg gac tac aac aat        960
Ala Thr Pro Cys Lys Tyr Glu Asp Ile Thr Ala Trp Asp Tyr Asn Asn
305                 310                 315                 320 ctc cgt atc gcg aaa ctg ttc agc taa                                    987
Leu Arg Ile Ala Lys Leu Phe Ser
                325

<210> SEQ ID NO 6
<211> LENGTH: 328
<212> TYPE: PRT
<213> ORGANISM: Penicillium chrysogenum Wisconsin 54-1255

<400> SEQUENCE: 6

Met Ser Gln Ala Leu Asp Leu Ser Leu Leu Lys Gly Ser Pro Glu Glu
1               5                   10                  15

Arg Asp Glu Val Ser Ala Ala Leu Leu Asp Thr Leu Lys Thr Arg Gly
                20                  25                  30

Val Ala Lys Leu Lys Asn His Gly Leu Pro Glu Asp Leu Ile Ala Glu
            35                  40                  45

Met Phe Asp Tyr Thr Arg Arg Phe Phe Ser Leu Ser Leu Glu Asp Lys
50                  55                  60

Met Thr Ala Lys His Pro Pro Glu Ala Asn Pro Asn Arg Gly Tyr Ser
65                  70                  75                  80

Tyr Val Gly Gln Glu Ser Val Ser Ser Ile Ser Gly Tyr Glu Lys Gly
                85                  90                  95

Leu Pro Gln Gly Lys Thr Ile Arg Asp Ile Lys Glu Thr Leu Asp Met
            100                 105                 110

Gly Ser Pro His Asp Ser Leu Val Asp Asn Ile Trp Val Ala Glu Glu
        115                 120                 125

Lys Leu Pro Gly Phe Arg Lys Phe Met Glu Asp Phe Tyr Glu Ser Cys
130                 135                 140

Phe Lys Val Glu Leu Glu Ile Leu Asp Ala Leu Ala Gln Ala Leu Glu
145                 150                 155                 160

Ile Ser Ala Pro Asp Leu Arg Leu Leu His Asn Lys Ala Glu Asn Glu
                165                 170                 175
```

```
Phe Arg Leu Leu His Tyr Pro Ala Val Pro Ala Ser Ala Leu Glu Asp
            180                 185                 190

Gly Thr Ala Thr Arg Ile Ala Glu His Thr Asp Phe Gly Thr Ile Thr
            195                 200                 205

Met Leu Phe Gln Asp Ser Thr Gly Gly Leu Gln Val Glu Asp Gln Thr
        210                 215                 220

Asn Leu Gly Thr Phe His Asp Val Val Ser Gly Gly Lys Ser Glu Ile
225                 230                 235                 240

Ile Leu Asn Ile Gly Asp Ser Leu Gln Arg Leu Thr Asn Asp Thr Phe
                245                 250                 255

Met Ala Ala Cys His Arg Val Thr Tyr Pro Pro Thr Val Lys Val Gly
            260                 265                 270

Ser Asp Val Val Ile Pro Glu Arg Tyr Ser Val Ala Tyr Phe Ala Lys
        275                 280                 285

Pro Asn Arg Ile Ala Ser Leu Phe Pro Leu Lys Lys Phe Ile Thr Pro
        290                 295                 300

Ala Thr Pro Cys Lys Tyr Glu Asp Ile Thr Ala Trp Asp Tyr Asn Asn
305                 310                 315                 320

Leu Arg Ile Ala Lys Leu Phe Ser
                325

<210> SEQ ID NO 7
<211> LENGTH: 1014
<212> TYPE: DNA
<213> ORGANISM: Gibberella zeae PH-1
<220> FEATURE:
<221> NAME/KEY: CDS
<222> LOCATION: (1)..(1014)

<400> SEQUENCE: 7 atg gct gcc ctg aac gtt gac acc ctg gac atg tcc ctt ttc ttc ggt      48
Met Ala Ala Leu Asn Val Asp Thr Leu Asp Met Ser Leu Phe Phe Gly
1               5                   10                  15 acc cct gat cag aag aaa gat ttc tgc gac tcg ctg ctg cgc ctg ctg      96
Thr Pro Asp Gln Lys Lys Asp Phe Cys Asp Ser Leu Leu Arg Leu Leu
            20                  25                  30 aaa aag cgt ggc ggt gtg aag ctc gtt aac cac tct att ccg agc gag    144
Lys Lys Arg Gly Gly Val Lys Leu Val Asn His Ser Ile Pro Ser Glu
        35                  40                  45 gat atc cat gag ctg ttt gcc caa acc aaa cgc ttc ttt gaa ctg ccg    192
Asp Ile His Glu Leu Phe Ala Gln Thr Lys Arg Phe Phe Glu Leu Pro
    50                  55                  60 ctg gaa acg aaa atg att gcg aaa cat ccg cca cag gcg aat ccg aac    240
Leu Glu Thr Lys Met Ile Ala Lys His Pro Pro Gln Ala Asn Pro Asn
65                  70                  75                  80 cgt ggt tac agc ttc gtg ggc cag gaa aac gtg gcg aat atc tcc ggt    288
Arg Gly Tyr Ser Phe Val Gly Gln Glu Asn Val Ala Asn Ile Ser Gly
                85                  90                  95 tac gag aag ggt ctg ggc cca caa acc acg cgt gac att aaa gag act    336
Tyr Glu Lys Gly Leu Gly Pro Gln Thr Thr Arg Asp Ile Lys Glu Thr
            100                 105                 110 gtt gat ttc ggt agc gcg acg gac gag ctg gtc gac aat atc tgg gtt    384
Val Asp Phe Gly Ser Ala Thr Asp Glu Leu Val Asp Asn Ile Trp Val
        115                 120                 125 ccg gag gac aaa ctg ccg ggt ttt cgc aag ttc atg gaa ggt ttc tac    432
Pro Glu Asp Lys Leu Pro Gly Phe Arg Lys Phe Met Glu Gly Phe Tyr
    130                 135                 140 gaa aag gcg ttt aag acc gaa atg cag ctg ttg gaa gct ttg gct atc    480
```

```
Glu Lys Ala Phe Lys Thr Glu Met Gln Leu Leu Glu Ala Leu Ala Ile
145                 150                 155                 160 gca ctg ggc gtt tca gca gac cac ctg aaa agc atc cac aat cgt gct      528
Ala Leu Gly Val Ser Ala Asp His Leu Lys Ser Ile His Asn Arg Ala
            165                 170                 175 gaa aac gag ttt cgt atc ttg cac tat ccg gca gtg ccg gcg tcc gag      576
Glu Asn Glu Phe Arg Ile Leu His Tyr Pro Ala Val Pro Ala Ser Glu
        180                 185                 190 ctg gcg gat ggc act gca acg cgc atc gca gag cac acc gat ttc ggt      624
Leu Ala Asp Gly Thr Ala Thr Arg Ile Ala Glu His Thr Asp Phe Gly
            195                 200                 205 acc att acg atg ctg ttc cag gac agc gtc ggt ggc tta cag gtc gaa      672
Thr Ile Thr Met Leu Phe Gln Asp Ser Val Gly Gly Leu Gln Val Glu
        210                 215                 220 gat caa gag aat ttg ggc cat ttc aac aac gtg gag agc gcg gca ccg      720
Asp Gln Glu Asn Leu Gly His Phe Asn Asn Val Glu Ser Ala Ala Pro
225                 230                 235                 240 acg gac att atc ctg aat att ggc gac agc ctg caa cgt ctg acc aat      768
Thr Asp Ile Ile Leu Asn Ile Gly Asp Ser Leu Gln Arg Leu Thr Asn
            245                 250                 255 gat acc ttt aaa gcc gcg tgt cat cgt gtc acc tac cct ccg agc att      816
Asp Thr Phe Lys Ala Ala Cys His Arg Val Thr Tyr Pro Pro Ser Ile
        260                 265                 270 aag gcg agc gac ggt gaa caa gtt att ccg gag cgc tat agc atc gcc      864
Lys Ala Ser Asp Gly Glu Gln Val Ile Pro Glu Arg Tyr Ser Ile Ala
            275                 280                 285 tat ttt gca aag ccg aac cgt tct gcc agc ctg ttc ccg ctg aaa gag      912
Tyr Phe Ala Lys Pro Asn Arg Ser Ala Ser Leu Phe Pro Leu Lys Glu
        290                 295                 300 ttt att gag gaa ggt atg ccg tgc aag tac gaa gat gtc acc gcg tgg      960
Phe Ile Glu Glu Gly Met Pro Cys Lys Tyr Glu Asp Val Thr Ala Trp
305                 310                 315                 320 gag tgg aat aac cgt cgt atc gag aag ctg ttt agc agc gat gcg aaa     1008
Glu Trp Asn Asn Arg Arg Ile Glu Lys Leu Phe Ser Ser Asp Ala Lys
            325                 330                 335 gcg taa                                                              1014
Ala

<210> SEQ ID NO 8
<211> LENGTH: 337
<212> TYPE: PRT
<213> ORGANISM: Gibberella zeae PH-1

<400> SEQUENCE: 8

Met Ala Ala Leu Asn Val Asp Thr Leu Asp Met Ser Leu Phe Phe Gly
1               5                   10                  15

Thr Pro Asp Gln Lys Lys Asp Phe Cys Asp Ser Leu Leu Arg Leu Leu
            20                  25                  30

Lys Lys Arg Gly Gly Val Lys Leu Val Asn His Ser Ile Pro Ser Glu
        35                  40                  45

Asp Ile His Glu Leu Phe Ala Gln Thr Lys Arg Phe Phe Glu Leu Pro
    50                  55                  60

Leu Glu Thr Lys Met Ile Ala Lys His Pro Gln Ala Asn Pro Asn
65                  70                  75                  80

Arg Gly Tyr Ser Phe Val Gly Gln Glu Asn Val Ala Asn Ile Ser Gly
                85                  90                  95

Tyr Glu Lys Gly Leu Gly Pro Gln Thr Thr Arg Asp Ile Lys Glu Thr
            100                 105                 110
```

```
Val Asp Phe Gly Ser Ala Thr Asp Glu Leu Val Asp Asn Ile Trp Val
            115                 120                 125

Pro Glu Asp Lys Leu Pro Gly Phe Arg Lys Phe Met Glu Gly Phe Tyr
        130                 135                 140

Glu Lys Ala Phe Lys Thr Glu Met Gln Leu Leu Glu Ala Leu Ala Ile
145                 150                 155                 160

Ala Leu Gly Val Ser Ala Asp His Leu Lys Ser Ile His Asn Arg Ala
                165                 170                 175

Glu Asn Glu Phe Arg Ile Leu His Tyr Pro Ala Val Pro Ala Ser Glu
            180                 185                 190

Leu Ala Asp Gly Thr Ala Thr Arg Ile Ala Glu His Thr Asp Phe Gly
        195                 200                 205

Thr Ile Thr Met Leu Phe Gln Asp Ser Val Gly Gly Leu Gln Val Glu
    210                 215                 220

Asp Gln Glu Asn Leu Gly His Phe Asn Asn Val Glu Ser Ala Ala Pro
225                 230                 235                 240

Thr Asp Ile Ile Leu Asn Ile Gly Asp Ser Leu Gln Arg Leu Thr Asn
                245                 250                 255

Asp Thr Phe Lys Ala Ala Cys His Arg Val Thr Tyr Pro Pro Ser Ile
            260                 265                 270

Lys Ala Ser Asp Gly Glu Gln Val Ile Pro Glu Arg Tyr Ser Ile Ala
        275                 280                 285

Tyr Phe Ala Lys Pro Asn Arg Ser Ala Ser Leu Phe Pro Leu Lys Glu
    290                 295                 300

Phe Ile Glu Glu Gly Met Pro Cys Lys Tyr Glu Asp Val Thr Ala Trp
305                 310                 315                 320

Glu Trp Asn Asn Arg Arg Ile Glu Lys Leu Phe Ser Ser Asp Ala Lys
                325                 330                 335

Ala

<210> SEQ ID NO 9
<211> LENGTH: 993
<212> TYPE: DNA
<213> ORGANISM: Colletotrichum gloeosporioides Nara gc5
<220> FEATURE:
<221> NAME/KEY: CDS
<222> LOCATION: (1)..(993)

<400> SEQUENCE: 9 atg agc gat aaa ggt gca acg ttg gac atg agc ctg ttt ttc ggt acg       48
Met Ser Asp Lys Gly Ala Thr Leu Asp Met Ser Leu Phe Phe Gly Thr
1               5                   10                  15 cca gag gaa aaa ggc tat ttc tgt acc gaa ctg ttg cgt ctg ctg aag       96
Pro Glu Glu Lys Gly Tyr Phe Cys Thr Glu Leu Leu Arg Leu Leu Lys
            20                  25                  30 ttg cgt ggt ggt gtt aag att cag aat cac tct atc ccg gac gaa gat      144
Leu Arg Gly Gly Val Lys Ile Gln Asn His Ser Ile Pro Asp Glu Asp
        35                  40                  45 atc cac aag ctg ttc gac atg agc cgt aag ttt ttc gcc tta ccg ctg      192
Ile His Lys Leu Phe Asp Met Ser Arg Lys Phe Phe Ala Leu Pro Leu
    50                  55                  60 gag act aaa atg gaa gcg aaa cat ccg ccg caa gct aat ccg aac cgc      240
Glu Thr Lys Met Glu Ala Lys His Pro Pro Gln Ala Asn Pro Asn Arg
65                  70                  75                  80 ggc tac agc ttt atc ggc cag gag aat gtc gcc aac atc agc ggt tac      288
Gly Tyr Ser Phe Ile Gly Gln Glu Asn Val Ala Asn Ile Ser Gly Tyr
                85                  90                  95
```

-continued

```
gag aaa ggc ctg ggc cct ggt aag acc cgt gat atc aaa gaa acc ctg      336
Glu Lys Gly Leu Gly Pro Gly Lys Thr Arg Asp Ile Lys Glu Thr Leu
            100                 105                 110 gac atg ggt tcc gca cag gat gat ttg gtc gac aac ctg tgg att ccg      384
Asp Met Gly Ser Ala Gln Asp Asp Leu Val Asp Asn Leu Trp Ile Pro
        115                 120                 125 gag gaa agc ctg ccg ggt ttt cgt ggc ttt atg gaa tcc ttc tac gaa      432
Glu Glu Ser Leu Pro Gly Phe Arg Gly Phe Met Glu Ser Phe Tyr Glu
    130                 135                 140 aaa gca ttc aag acc gaa atg caa ctc ctg agc gcg ttg gca att gcg      480
Lys Ala Phe Lys Thr Glu Met Gln Leu Leu Ser Ala Leu Ala Ile Ala
145                 150                 155                 160 ctg ggt gtt tcg gag gac cac atg aaa acg ctg cac aat cgc gcg gag      528
Leu Gly Val Ser Glu Asp His Met Lys Thr Leu His Asn Arg Ala Glu
                165                 170                 175 aac gag ttc cgt ctg ctg cat tat ccg gct atc ccg gcg acc gag ctg      576
Asn Glu Phe Arg Leu Leu His Tyr Pro Ala Ile Pro Ala Thr Glu Leu
            180                 185                 190 gca gat ggt acc gcg acg cgc att gcc gaa cac acc gat ttt ggt acg      624
Ala Asp Gly Thr Ala Thr Arg Ile Ala Glu His Thr Asp Phe Gly Thr
        195                 200                 205 att acc atg ctg ttt caa gac agc gtc ggc ggt ctg caa gtg gag gac      672
Ile Thr Met Leu Phe Gln Asp Ser Val Gly Gly Leu Gln Val Glu Asp
    210                 215                 220 caa acc cag ccg ggt gtg ttc cgt agc gtg gag agc gaa aag ccg acc      720
Gln Thr Gln Pro Gly Val Phe Arg Ser Val Glu Ser Glu Lys Pro Thr
225                 230                 235                 240 gat atc att ctg aat atc ggc gac agc ctg cag cgc ctg acc aat gac      768
Asp Ile Ile Leu Asn Ile Gly Asp Ser Leu Gln Arg Leu Thr Asn Asp
                245                 250                 255 acg ttc aga gcg gcg tgc cac cgt gtc acg tac ccg cca gct att aag      816
Thr Phe Arg Ala Ala Cys His Arg Val Thr Tyr Pro Pro Ala Ile Lys
            260                 265                 270 gcg cgt gat aac gtg cag atc ccg gag cgc tat agc att gca tac ttt      864
Ala Arg Asp Asn Val Gln Ile Pro Glu Arg Tyr Ser Ile Ala Tyr Phe
        275                 280                 285 gtt aaa cct aac cgt cat gcc tct ctg ctt ccg ctg aaa gag ttc atc      912
Val Lys Pro Asn Arg His Ala Ser Leu Leu Pro Leu Lys Glu Phe Ile
    290                 295                 300 acc gac gcg acc ccg tgc cgt tat gaa gat gtt acg gcg tgg gag tgg      960
Thr Asp Ala Thr Pro Cys Arg Tyr Glu Asp Val Thr Ala Trp Glu Trp
305                 310                 315                 320 aac aat cgc cgt att act aag ctg ttt ggc taa                          993
Asn Asn Arg Arg Ile Thr Lys Leu Phe Gly
                325                 330
```

<210> SEQ ID NO 10
<211> LENGTH: 330
<212> TYPE: PRT
<213> ORGANISM: Colletotrichum gloeosporioides Nara gc5

<400> SEQUENCE: 10

```
Met Ser Asp Lys Gly Ala Thr Leu Asp Met Ser Leu Phe Phe Gly Thr
1               5                   10                  15

Pro Glu Glu Lys Gly Tyr Phe Cys Thr Glu Leu Leu Arg Leu Leu Lys
            20                  25                  30

Leu Arg Gly Gly Val Lys Ile Gln Asn His Ser Ile Pro Asp Glu Asp
        35                  40                  45

Ile His Lys Leu Phe Asp Met Ser Arg Lys Phe Phe Ala Leu Pro Leu
    50                  55                  60
```

```
Glu Thr Lys Met Glu Ala Lys His Pro Pro Gln Ala Asn Pro Asn Arg
 65                  70                  75                  80

Gly Tyr Ser Phe Ile Gly Gln Glu Asn Val Ala Asn Ile Ser Gly Tyr
                 85                  90                  95

Glu Lys Gly Leu Gly Pro Gly Lys Thr Arg Asp Ile Lys Glu Thr Leu
            100                 105                 110

Asp Met Gly Ser Ala Gln Asp Asp Leu Val Asp Asn Leu Trp Ile Pro
        115                 120                 125

Glu Glu Ser Leu Pro Gly Phe Arg Gly Phe Met Glu Ser Phe Tyr Glu
    130                 135                 140

Lys Ala Phe Lys Thr Glu Met Gln Leu Leu Ser Ala Leu Ala Ile Ala
145                 150                 155                 160

Leu Gly Val Ser Glu Asp His Met Lys Thr Leu His Asn Arg Ala Glu
                165                 170                 175

Asn Glu Phe Arg Leu Leu His Tyr Pro Ala Ile Pro Ala Thr Glu Leu
            180                 185                 190

Ala Asp Gly Thr Ala Thr Arg Ile Ala Glu His Thr Asp Phe Gly Thr
        195                 200                 205

Ile Thr Met Leu Phe Gln Asp Ser Val Gly Gly Leu Gln Val Glu Asp
    210                 215                 220

Gln Thr Gln Pro Gly Val Phe Arg Ser Val Glu Ser Glu Lys Pro Thr
225                 230                 235                 240

Asp Ile Ile Leu Asn Ile Gly Asp Ser Leu Gln Arg Leu Thr Asn Asp
                245                 250                 255

Thr Phe Arg Ala Ala Cys His Arg Val Thr Tyr Pro Pro Ala Ile Lys
            260                 265                 270

Ala Arg Asp Asn Val Gln Ile Pro Glu Arg Tyr Ser Ile Ala Tyr Phe
        275                 280                 285

Val Lys Pro Asn Arg His Ala Ser Leu Leu Pro Leu Lys Glu Phe Ile
    290                 295                 300

Thr Asp Ala Thr Pro Cys Arg Tyr Glu Asp Val Thr Ala Trp Glu Trp
305                 310                 315                 320

Asn Asn Arg Arg Ile Thr Lys Leu Phe Gly
                325                 330

<210> SEQ ID NO 11
<211> LENGTH: 1026
<212> TYPE: DNA
<213> ORGANISM: Emericella nidulans FGSC A4
<220> FEATURE:
<221> NAME/KEY: CDS
<222> LOCATION: (1)..(1026)

<400> SEQUENCE: 11 atg gat atc ccg acc ctg aat ttt cgt gac ttc acc agc ggt acc cag     48
Met Asp Ile Pro Thr Leu Asn Phe Arg Asp Phe Thr Ser Gly Thr Gln
  1               5                  10                  15 agc caa cgt gac acg ttt tgt agc aac ctg tac acc tcc ctg agc acg     96
Ser Gln Arg Asp Thr Phe Cys Ser Asn Leu Tyr Thr Ser Leu Ser Thr
                 20                  25                  30 ctg ggc ttc gtg aaa atc aag aac cac acg att ccg gat gag att tta    144
Leu Gly Phe Val Lys Ile Lys Asn His Thr Ile Pro Asp Glu Ile Leu
             35                  40                  45 gac cag gtg ttt gat tgg tct aaa cac ttc ttt gcg ctg ccg ctg gag    192
Asp Gln Val Phe Asp Trp Ser Lys His Phe Phe Ala Leu Pro Leu Glu
         50                  55                  60
```

| | | |
|---|---|---|
| tcc aaa act ctg gca gcg cat ccg gtc caa gca aac cca cat cgt ggc<br>Ser Lys Thr Leu Ala Ala His Pro Val Gln Ala Asn Pro His Arg Gly<br>65                      70                      75                      80 | 240 |
| tgg tcc tgt gtc ggc cag gag aag ctg agc gtt att cgc cag ggt aag<br>Trp Ser Cys Val Gly Gln Glu Lys Leu Ser Val Ile Arg Gln Gly Lys<br>                      85                      90                      95 | 288 |
| gca gtg ttc gat ctg aaa gaa agc ttc gat ctg ggt ccg gaa aat gac<br>Ala Val Phe Asp Leu Lys Glu Ser Phe Asp Leu Gly Pro Glu Asn Asp<br>100                     105                   110 | 336 |
| ccg ctg tat cct aat atc ttc ccg gac gat tcg gtc atc ccg ggt ttt<br>Pro Leu Tyr Pro Asn Ile Phe Pro Asp Asp Ser Val Ile Pro Gly Phe<br>            115                   120                   125 | 384 |
| cgt ccg ttc atg gag agc ttt tac gcc caa tgc caa gcc ctg cac ttg<br>Arg Pro Phe Met Glu Ser Phe Tyr Ala Gln Cys Gln Ala Leu His Leu<br>130                     135                   140 | 432 |
| act ctt ctg tcc gcc att gca ctg agc ctg aat cag gat gca agc ttc<br>Thr Leu Leu Ser Ala Ile Ala Leu Ser Leu Asn Gln Asp Ala Ser Phe<br>145                     150                   155                   160 | 480 |
| ctg agc gac cgt tgc ggt acg aac agc tca gag ctg cgc ctg aac cac<br>Leu Ser Asp Arg Cys Gly Thr Asn Ser Ser Glu Leu Arg Leu Asn His<br>                     165                   170                   175 | 528 |
| tat cct gcg acc aag att agc gat ttg cag tct ggc aaa aag atg cgt<br>Tyr Pro Ala Thr Lys Ile Ser Asp Leu Gln Ser Gly Lys Lys Met Arg<br>180                     185                   190 | 576 |
| att agc tct cat acg gac ttt ggc acg att acc ctg ttg tgg cag gac<br>Ile Ser Ser His Thr Asp Phe Gly Thr Ile Thr Leu Leu Trp Gln Asp<br>                     195                   200                   205 | 624 |
| ggt gtt ggt ggt ctg gaa gtg gag gat caa aat cac gag ggt gtc tac<br>Gly Val Gly Gly Leu Glu Val Glu Asp Gln Asn His Glu Gly Val Tyr<br>210                     215                   220 | 672 |
| ttg ccg gtc ggc ccg acc agc acc gaa tcg agc agc ggt gcg gac acc<br>Leu Pro Val Gly Pro Thr Ser Thr Glu Ser Ser Ser Gly Ala Asp Thr<br>225                     230                   235                   240 | 720 |
| gac tgt gac agc ggt cgc gag atg atc gtg aac gtt ggc gac tgc ctg<br>Asp Cys Asp Ser Gly Arg Glu Met Ile Val Asn Val Gly Asp Cys Leu<br>                     245                   250                   255 | 768 |
| cag cgt tgg acc aac gat cgt ctg cgt agc gcg aac cac cgc gtt acc<br>Gln Arg Trp Thr Asn Asp Arg Leu Arg Ser Ala Asn His Arg Val Thr<br>260                     265                   270 | 816 |
| ctg ccg gct gaa atg aaa gac aag agc cgt ccg gag atc agc aat gac<br>Leu Pro Ala Glu Met Lys Asp Lys Ser Arg Pro Glu Ile Ser Asn Asp<br>            275                   280                   285 | 864 |
| ctc gtt ccg gat cgc tat agc gtt gcg tac ttc ggt aaa cca gat cgt<br>Leu Val Pro Asp Arg Tyr Ser Val Ala Tyr Phe Gly Lys Pro Asp Arg<br>290                     295                   300 | 912 |
| ggt gcg ctg gtg gcc gct atc ccg gaa ctg gtt gag gaa ggc gaa gaa<br>Gly Ala Leu Val Ala Ala Ile Pro Glu Leu Val Glu Glu Gly Glu Glu<br>305                     310                   315                   320 | 960 |
| gtg cgt tac aag ggt ggc atg acc gcg tgg gag tac aat cag agc cgc<br>Val Arg Tyr Lys Gly Gly Met Thr Ala Trp Glu Tyr Asn Gln Ser Arg<br>                     325                   330                   335 | 1008 |
| ctg ttg caa acg tat taa<br>Leu Leu Gln Thr Tyr<br>340 | 1026 |

<210> SEQ ID NO 12
<211> LENGTH: 341
<212> TYPE: PRT
<213> ORGANISM: Emericella nidulans FGSC A4

<400> SEQUENCE: 12

```
Met Asp Ile Pro Thr Leu Asn Phe Arg Asp Phe Thr Ser Gly Thr Gln
 1               5                  10                  15

Ser Gln Arg Asp Thr Phe Cys Ser Asn Leu Tyr Thr Ser Leu Ser Thr
            20                  25                  30

Leu Gly Phe Val Lys Ile Lys Asn His Thr Ile Pro Asp Glu Ile Leu
        35                  40                  45

Asp Gln Val Phe Asp Trp Ser Lys His Phe Ala Leu Pro Leu Glu
    50                  55                  60

Ser Lys Thr Leu Ala Ala His Pro Val Gln Ala Asn Pro His Arg Gly
65                  70                  75                  80

Trp Ser Cys Val Gly Gln Glu Lys Leu Ser Val Ile Arg Gln Gly Lys
                85                  90                  95

Ala Val Phe Asp Leu Lys Glu Ser Phe Asp Leu Gly Pro Glu Asn Asp
                100                 105                 110

Pro Leu Tyr Pro Asn Ile Phe Pro Asp Ser Val Ile Pro Gly Phe
        115                 120                 125

Arg Pro Phe Met Glu Ser Phe Tyr Ala Gln Cys Gln Ala Leu His Leu
    130                 135                 140

Thr Leu Leu Ser Ala Ile Ala Leu Ser Leu Asn Gln Asp Ala Ser Phe
145                 150                 155                 160

Leu Ser Asp Arg Cys Gly Thr Asn Ser Ser Glu Leu Arg Leu Asn His
                165                 170                 175

Tyr Pro Ala Thr Lys Ile Ser Asp Leu Gln Ser Gly Lys Lys Met Arg
                180                 185                 190

Ile Ser Ser His Thr Asp Phe Gly Thr Ile Thr Leu Leu Trp Gln Asp
            195                 200                 205

Gly Val Gly Gly Leu Glu Val Glu Asp Gln Asn His Glu Gly Val Tyr
            210                 215                 220

Leu Pro Val Gly Pro Thr Ser Thr Glu Ser Ser Ser Gly Ala Asp Thr
225                 230                 235                 240

Asp Cys Asp Ser Gly Arg Glu Met Ile Val Asn Val Gly Asp Cys Leu
                245                 250                 255

Gln Arg Trp Thr Asn Asp Arg Leu Arg Ser Ala Asn His Arg Val Thr
                260                 265                 270

Leu Pro Ala Glu Met Lys Asp Lys Ser Arg Pro Glu Ile Ser Asn Asp
            275                 280                 285

Leu Val Pro Asp Arg Tyr Ser Val Ala Tyr Phe Gly Lys Pro Asp Arg
            290                 295                 300

Gly Ala Leu Val Ala Ala Ile Pro Glu Leu Val Glu Glu Gly Glu Glu
305                 310                 315                 320

Val Arg Tyr Lys Gly Gly Met Thr Ala Trp Glu Tyr Asn Gln Ser Arg
                325                 330                 335

Leu Leu Gln Thr Tyr
            340
```

<210> SEQ ID NO 13
<211> LENGTH: 28
<212> TYPE: DNA
<213> ORGANISM: Artificial Sequence
<220> FEATURE:
<223> OTHER INFORMATION: PCR primer

<400> SEQUENCE: 13
aaggatccat ggccgccctc aacgcaga                28

<210> SEQ ID NO 14
<211> LENGTH: 28
<212> TYPE: DNA
<213> ORGANISM: Artificial Sequence
<220> FEATURE:
<223> OTHER INFORMATION: PCR primer

<400> SEQUENCE: 14 ccaagcttttt aagccttagc ttcagcag                                          28

<210> SEQ ID NO 15
<211> LENGTH: 756
<212> TYPE: DNA
<213> ORGANISM: Unknown
<220> FEATURE:
<223> OTHER INFORMATION: environmental
<220> FEATURE:
<221> NAME/KEY: CDS
<222> LOCATION: (1)..(753)

<400> SEQUENCE: 15

```
atg acc acc gcc gcc ttc acg cct ccc ttc atc gat ccc gcc gaa ctg       48
Met Thr Thr Ala Ala Phe Thr Pro Pro Phe Ile Asp Pro Ala Glu Leu
1               5                   10                  15 ccc gcc gcg ctg cgc gag cag ggc tac gcg gtg ctg agc ccc caa ggc       96
Pro Ala Ala Leu Arg Glu Gln Gly Tyr Ala Val Leu Ser Pro Gln Gly
            20                  25                  30 gtc agc gac tgg ctc ggc gca ccg ctt gcg caa ctc gag gca ctg cac      144
Val Ser Asp Trp Leu Gly Ala Pro Leu Ala Gln Leu Glu Ala Leu His
        35                  40                  45 gcg gac tgg aac aac ctt cca ccc gac gac tac ctg aag gac ggc ggc      192
Ala Asp Trp Asn Asn Leu Pro Pro Asp Asp Tyr Leu Lys Asp Gly Gly
    50                  55                  60 cgc tac cgc acg cgc cgc cat gca tgc ttc acc gtc gag gcc ggc gac      240
Arg Tyr Arg Thr Arg Arg His Ala Cys Phe Thr Val Glu Ala Gly Asp
65                  70                  75                  80 aac gcc acg ctc gaa cag gtg ccg cat cgc gcg cac tgg cag ccg gtc      288
Asn Ala Thr Leu Glu Gln Val Pro His Arg Ala His Trp Gln Pro Val
                85                  90                  95 gaa tac aac gcg ctg cac ggg ggc atg cag cgc tgg ttt gcg ccg atg      336
Glu Tyr Asn Ala Leu His Gly Gly Met Gln Arg Trp Phe Ala Pro Met
            100                 105                 110 ctg gcc gag acc atc gtg cag cca gtg tgg caa cgc ctg ctg cag cgc      384
Leu Ala Glu Thr Ile Val Gln Pro Val Trp Gln Arg Leu Leu Gln Arg
        115                 120                 125 ctc ggt acg gcc gcg agc gac atg cgg ggt acg cca cag aaa tgg ttt      432
Leu Gly Thr Ala Ala Ser Asp Met Arg Gly Thr Pro Gln Lys Trp Phe
    130                 135                 140 gtc gag gcg cat caa ttc cgc atc gac acc gca ggc ggc atc ggc cgt      480
Val Glu Ala His Gln Phe Arg Ile Asp Thr Ala Gly Gly Ile Gly Arg
145                 150                 155                 160 ccg acc ccc gag ggc gcg cac cgc gac ggc gtc gac ctg gtg gcc gtc      528
Pro Thr Pro Glu Gly Ala His Arg Asp Gly Val Asp Leu Val Ala Val
                165                 170                 175 gcg ttg gtc ggt cgt caa ggc atc aag ggc ggc gag acg cgc gtg ttc      576
Ala Leu Val Gly Arg Gln Gly Ile Lys Gly Gly Glu Thr Arg Val Phe
            180                 185                 190 gag gcc aac ggc cgt cgc ggc gag cga ttc acc atg acc gag ccc tgg      624
Glu Ala Asn Gly Arg Arg Gly Glu Arg Phe Thr Met Thr Glu Pro Trp
        195                 200                 205 acg ctg ctc ctg ctc gac gac gca cgc gtc att cac gaa tcg acg ccg      672
Thr Leu Leu Leu Leu Asp Asp Ala Arg Val Ile His Glu Ser Thr Pro
```

```
                        210                 215                 220
atc cag cca ctc gaa gag ggc ggt gcg ggt tgg cgc gat acg ctc gtg      720
Ile Gln Pro Leu Glu Glu Gly Gly Ala Gly Trp Arg Asp Thr Leu Val
225                 230                 235                 240 atc acc tgc cga tcg caa ggt ttc cag ggc gat taa                      756
Ile Thr Cys Arg Ser Gln Gly Phe Gln Gly Asp
                245                 250
```

<210> SEQ ID NO 16
<211> LENGTH: 251
<212> TYPE: PRT
<213> ORGANISM: Unknown
<220> FEATURE:
<223> OTHER INFORMATION: environmental

<400> SEQUENCE: 16

```
Met Thr Thr Ala Ala Phe Thr Pro Pro Phe Ile Asp Pro Ala Glu Leu
1               5                   10                  15

Pro Ala Ala Leu Arg Glu Gln Gly Tyr Ala Val Leu Ser Pro Gln Gly
                20                  25                  30

Val Ser Asp Trp Leu Gly Ala Pro Leu Ala Gln Leu Glu Ala Leu His
            35                  40                  45

Ala Asp Trp Asn Asn Leu Pro Pro Asp Asp Tyr Leu Lys Asp Gly Gly
        50                  55                  60

Arg Tyr Arg Thr Arg Arg His Ala Cys Phe Thr Val Glu Ala Gly Asp
65                  70                  75                  80

Asn Ala Thr Leu Glu Gln Val Pro His Arg Ala His Trp Gln Pro Val
                85                  90                  95

Glu Tyr Asn Ala Leu His Gly Gly Met Gln Arg Trp Phe Ala Pro Met
            100                 105                 110

Leu Ala Glu Thr Ile Val Gln Pro Val Trp Gln Arg Leu Leu Gln Arg
        115                 120                 125

Leu Gly Thr Ala Ala Ser Asp Met Arg Gly Thr Pro Gln Lys Trp Phe
    130                 135                 140

Val Glu Ala His Gln Phe Arg Ile Asp Thr Ala Gly Gly Ile Gly Arg
145                 150                 155                 160

Pro Thr Pro Glu Gly Ala His Arg Asp Gly Val Asp Leu Val Ala Val
                165                 170                 175

Ala Leu Val Gly Arg Gln Gly Ile Lys Gly Gly Glu Thr Arg Val Phe
            180                 185                 190

Glu Ala Asn Gly Arg Arg Gly Glu Arg Phe Thr Met Thr Glu Pro Trp
        195                 200                 205

Thr Leu Leu Leu Leu Asp Asp Ala Arg Val Ile His Glu Ser Thr Pro
    210                 215                 220

Ile Gln Pro Leu Glu Glu Gly Gly Ala Gly Trp Arg Asp Thr Leu Val
225                 230                 235                 240

Ile Thr Cys Arg Ser Gln Gly Phe Gln Gly Asp
                245                 250
```

<210> SEQ ID NO 17
<211> LENGTH: 840
<212> TYPE: DNA
<213> ORGANISM: Unknown
<220> FEATURE:
<223> OTHER INFORMATION: environmental
<220> FEATURE:
<221> NAME/KEY: CDS
<222> LOCATION: (1)..(837)

```
<400> SEQUENCE: 17 atg gaa gtg cca aat tcc agc ttc aat acg aat tcg ccg tta cgg gag      48
Met Glu Val Pro Asn Ser Ser Phe Asn Thr Asn Ser Pro Leu Arg Glu
1               5                   10                  15 tcg atc tct tcg att gta atg aaa ggg tat gcg att cta aaa att cca      96
Ser Ile Ser Ser Ile Val Met Lys Gly Tyr Ala Ile Leu Lys Ile Pro
            20                  25                  30 gtc cat gcg caa aca gcc atg tgg aag gtg ttg gac aac atc gac tcg     144
Val His Ala Gln Thr Ala Met Trp Lys Val Leu Asp Asn Ile Asp Ser
        35                  40                  45 gtt tcg cct gat ctt cgg cga gac ttc agt ttt ccg gag gtt acc gat     192
Val Ser Pro Asp Leu Arg Arg Asp Phe Ser Phe Pro Glu Val Thr Asp
    50                  55                  60 gga ttt tta tct gtc ggc ggt gag tac gcc aag tac acc agc agc atc     240
Gly Phe Leu Ser Val Gly Gly Glu Tyr Ala Lys Tyr Thr Ser Ser Ile
65                  70                  75                  80 gat ttg tgc gat cgc ttc tgc ttc tgg cat aag aat cgt gaa atg cat     288
Asp Leu Cys Asp Arg Phe Cys Phe Trp His Lys Asn Arg Glu Met His
                85                  90                  95 caa ggg aaa gaa ttc gca aac gac gaa gtc tat agg acc ata aag acc     336
Gln Gly Lys Glu Phe Ala Asn Asp Glu Val Tyr Arg Thr Ile Lys Thr
            100                 105                 110 tgc gag atg gaa atg cac acc atg gcg cag caa ttg att tcg gag ttg     384
Cys Glu Met Glu Met His Thr Met Ala Gln Gln Leu Ile Ser Glu Leu
        115                 120                 125 tgg gac ttt ttc aat agc ccc gat ccg gtg aat att cga gac agc tcg     432
Trp Asp Phe Phe Asn Ser Pro Asp Pro Val Asn Ile Arg Asp Ser Ser
    130                 135                 140 tat ctg cag ttg tgc atg tac gca agt cag tac cac gcg aat gat cgc     480
Tyr Leu Gln Leu Cys Met Tyr Ala Ser Gln Tyr His Ala Asn Asp Arg
145                 150                 155                 160 ggc tat ctg cag gac cgc cat gaa gat ggg cat ttg atc acg ctg atc     528
Gly Tyr Leu Gln Asp Arg His Glu Asp Gly His Leu Ile Thr Leu Ile
                165                 170                 175 aaa ccg acg cgc gat ggc ctc gtc att ttc cct ggc ggc ccg gaa gac     576
Lys Pro Thr Arg Asp Gly Leu Val Ile Phe Pro Gly Gly Pro Glu Asp
            180                 185                 190 tgc gaa gtt cca gta ttt ctg cgt gat gat gaa ttg ctc gtt att gca     624
Cys Glu Val Pro Val Phe Leu Arg Asp Asp Glu Leu Leu Val Ile Ala
        195                 200                 205 ggg tca ctg ctg acg gca atg tcg gat gga aga att ccc ccg atg tat     672
Gly Ser Leu Leu Thr Ala Met Ser Asp Gly Arg Ile Pro Pro Met Tyr
    210                 215                 220 cac gcc gtt aaa aat cca ttt gtg cag atg gaa aga aaa tcc gtt gtg     720
His Ala Val Lys Asn Pro Phe Val Gln Met Glu Arg Lys Ser Val Val
225                 230                 235                 240 tat ttt gcc att ccg gat ctt tcg cag acc tat acg aca ttg ctc gcc     768
Tyr Phe Ala Ile Pro Asp Leu Ser Gln Thr Tyr Thr Thr Leu Leu Ala
                245                 250                 255 aaa aat ccg atc aat gtc gga gaa ttg gcg gat gaa agt cac cgg gcc     816
Lys Asn Pro Ile Asn Val Gly Glu Leu Ala Asp Glu Ser His Arg Ala
            260                 265                 270 ttc ggc aat acg gcc ttg atc taa                                     840
Phe Gly Asn Thr Ala Leu Ile
        275

<210> SEQ ID NO 18
<211> LENGTH: 279
<212> TYPE: PRT
<213> ORGANISM: Unknown
```

```
<220> FEATURE:
<223> OTHER INFORMATION: environmental

<400> SEQUENCE: 18

Met Glu Val Pro Asn Ser Ser Phe Asn Thr Asn Ser Pro Leu Arg Glu
1               5                   10                  15

Ser Ile Ser Ser Ile Val Met Lys Gly Tyr Ala Ile Leu Lys Ile Pro
            20                  25                  30

Val His Ala Gln Thr Ala Met Trp Lys Val Leu Asp Asn Ile Asp Ser
        35                  40                  45

Val Ser Pro Asp Leu Arg Arg Asp Phe Ser Phe Pro Glu Val Thr Asp
    50                  55                  60

Gly Phe Leu Ser Val Gly Gly Glu Tyr Ala Lys Tyr Thr Ser Ser Ile
65                  70                  75                  80

Asp Leu Cys Asp Arg Phe Cys Phe Trp His Lys Asn Arg Glu Met His
                85                  90                  95

Gln Gly Lys Glu Phe Ala Asn Asp Glu Val Tyr Arg Thr Ile Lys Thr
            100                 105                 110

Cys Glu Met Glu Met His Thr Met Ala Gln Gln Leu Ile Ser Glu Leu
            115                 120                 125

Trp Asp Phe Phe Asn Ser Pro Asp Pro Val Asn Ile Arg Asp Ser Ser
    130                 135                 140

Tyr Leu Gln Leu Cys Met Tyr Ala Ser Gln Tyr His Ala Asn Asp Arg
145                 150                 155                 160

Gly Tyr Leu Gln Asp Arg His Glu Asp Gly His Leu Ile Thr Leu Ile
                165                 170                 175

Lys Pro Thr Arg Asp Gly Leu Val Ile Phe Pro Gly Gly Pro Glu Asp
            180                 185                 190

Cys Glu Val Pro Val Phe Leu Arg Asp Asp Glu Leu Leu Val Ile Ala
            195                 200                 205

Gly Ser Leu Leu Thr Ala Met Ser Asp Gly Arg Ile Pro Pro Met Tyr
    210                 215                 220

His Ala Val Lys Asn Pro Phe Val Gln Met Glu Arg Lys Ser Val Val
225                 230                 235                 240

Tyr Phe Ala Ile Pro Asp Leu Ser Gln Thr Tyr Thr Thr Leu Leu Ala
                245                 250                 255

Lys Asn Pro Ile Asn Val Gly Glu Leu Ala Asp Glu Ser His Arg Ala
            260                 265                 270

Phe Gly Asn Thr Ala Leu Ile
            275
```

PIPECOLINIC ACID 4-HYDROXYLASE AND METHOD FOR PRODUCING 4-HYDROXY AMINO ACID USING SAME

This is a divisional application of U.S. patent application Ser. No. 15/115,028, filed Jul. 28, 2016, which is the U.S. National Stage of PCT/JP2015/052126, filed Jan. 27, 2015, which claims priority of Japanese Application No. 2014-017716, filed Jan. 31, 2014, the disclosures of which are incorporated by reference herein in their entirety.

TECHNICAL FIELD

The present invention relates to a method for producing 4-hydroxy amino acid, which method utilizes a novel pipecolic acid 4-hydroxylase.

BACKGROUND ART

Amino acid hydroxylases are enzymes useful for production of intermediates of pharmaceuticals and the like, and the presence of proline 4-hydroxylase (Non-patent Document 1), L-isoleucine dioxygenase (Non-patent Document 2), and the like has been reported. In terms of enzymes having an ability to hydroxylate pipecolic acid, several kinds of proline hydroxylases have been reported to have an ability to hydroxylate 3-position or 5-position of L-pipecolic acid (Non-patent Document 3). However, no enzyme has so far been reported to hydroxylate 4-position of pipecolic acid.

The amino acid sequences of SEQ ID NOs: 2, 4, 6, 8, 10, and 12 are the same as GenBank accession NOs. EGU81245, XP_001827566, XP_002558179, XP_383389, ELA34460, and XP_659994, respectively, which are the amino acid sequences translated from the putative protein-coding DNA sequences based on genomic sequence information of the *Fusarium oxysporum* Fo5176 strain, *Aspergillus oryzae* RIB40 strain, *Penicillium chrysogenum* Wisconsin 54-1255 strain, *Gibberella zeae* (another name, *Fusarium graminearum*) PH-1 strain, *Colletotrichum gloeosporioides* Nara gc5 strain, and *Aspergillus nidulans* (another name, *Emericella nidulans*) FGSC A4, respectively. Since all of these proteins are derived from fungi, the proteins, if exist, are likely to be in a state where they have undergone glycosylation after their expression. However, there has been no report supporting their existence based on actual isolation or the like, and the functions of these proteins have been unknown at all.

Optically active 4-hydroxy amino acids are useful substances as intermediates of pharmaceuticals and the like. For example, (4S)-hydroxy-L-pipecolic acid can be used as a precursor of a Rho kinase inhibitor (Patent Document 1), and (4S)-hydroxy-D-pipecolic acid can be used as a precursor of CGS-20281, which is an NMDA receptor inhibitor (Non-patent Document 4). (4R)-Hydroxy-L-proline can be used as a precursor of icatibant acetate, which is a bradykinin B2 receptor inhibitor (Non-patent Document 5), and (4R)-hydroxy-D-proline can be used as a precursor of a factor Xa inhibitor (Patent Document 2). L-Homoserine can be used as a precursor of Omapatrilat, which is an ACE inhibitor (Patent Document 3), and 4-hydroxy-L-leucine can be used as a precursor of SCY-635, which is a cyclophilin inhibitor (Non-patent Document 6).

Examples of previously reported methods for synthesis of an optically active 4-hydroxy amino acid include a method in which (4S)-hydroxy-L-pipecolic acid or (4S)-hydroxy-D-pipecolic acid is produced by stereoselective cyclization of 3-butenol with an optically active C-aminocarbonyl nitrone or C-alkoxycarbonyl nitrone has been reported so far (Non-patent Document 7). A method in which (4R)-hydroxy-L-proline is synthesized from L-proline using proline 4-hydroxylase derived from the *Dactylosporangium* RH1 strain (Non-patent Document 1), and a method in which (4R)-hydroxy-D-proline is synthesized via an α,β-didehydroamino acid (Non-patent Document 8) have also been reported. A method in which L-homoserine is synthesized by fermentation using a recombinant *E. coli* (Patent Document 4), and a method in which 4-hydroxy-L-leucine is synthesized from L-leucine using L-isoleucine dioxygenase derived from the *Bacillus thuringiensis* 2e2 strain (Non-patent Document 2) have also been reported.

However, more efficient synthesis methods have been demanded since these methods have problems such as expensive materials, large numbers of steps, small numbers of the types of compounds to which the methods are applicable, and high purification loads.

PRIOR ART DOCUMENTS

Patent Documents

Patent Document 1: Japanese Translated PCT Patent Application Laid-open No. 2010-514720
Patent Document 2: Japanese Translated PCT Patent Application Laid-open No. 2009-526813
Patent Document 3: JP 7-48259 A
Patent Document 4: WO 2013/134625

Non-Patent Documents

Non-patent Document 1: Shibasaki et al., Appl. Environ. Microbiol., 1999, 65, 4028
Non-patent Document 2: Hibi et al., Appl. Environ. Microbiol., 2011, 77, 6926
Non-patent Document 3: Klein et al., Adv. Synth. Catal., 2011, 353, 1375
Non-patent Document 4: Occhiato et al., SYNTHESIS, 2009, 3611
Non-patent Document 5: Bork et al., Nat. Rev. Drug Discov., 2008, 7, 801
Non-patent Document 6: Hopkins et al., Antimicrobial. Agents Chemother., 2010, 54, 660
Non-patent Document 7: Cordero et al., Eur. J. Org. Chem., 2006, 3235
Non-patent Document 8: Kimura et al., Bull. Chem. Soc. Jpn., 2002, 75, 2517

SUMMARY OF THE INVENTION

Problems to be Solved by the Invention

An object of the present invention is to provide a novel pipecolic acid 4-hydroxylase, and a novel method for inexpensively and simply producing a 4-hydroxy amino acid, especially an optically active 4-hydroxy amino acid.

Means for Solving the Problems

In order to solve the problems described above, the present inventors intensively studied on a method for producing an optically active 4-hydroxy amino acid. As a result, the present inventors discovered that the protein FOXB_8233 derived from the *Fusarium oxysporum* Fo5176 strain, whose isolation as a protein has not been reported and whose function has been unknown, and its homologue proteins, have a 2-oxoglutaric acid-dependent pipecolic acid 4-hydroxylase activity. The present inventors then discovered that, by preparing transformants using DNAs encoding these proteins and reacting the prepared transformant cells, treated products thereof, and/or culture liquids thereof with various amino acids, various optically active 4-hydroxy amino acid can be obtained at high optical purity. The present invention was achieved based on these discoveries.

That is, the present invention can be summarized as follows.

[1] A pipecolic acid 4-hydroxylase protein having activity to react with L-pipecolic acid in the presence of 2-oxoglutaric acid and iron(II) ions, to produce trans-4-hydroxy-L-pipecolic acid.

[2] The pipecolic acid 4-hydroxylase protein according to [1], selected from the group consisting of the following (A), (B), and (C):

(A) a polypeptide comprising the amino acid sequence represented by SEQ ID NO:2, 4, 6, 8, 10, 12, 16, or 18;

(B) a polypeptide comprising the amino acid sequence represented by SEQ ID NO:2, 4, 6, 8, 10, 12, 16, or 18 except that one or several amino acids are deleted, substituted, and/or added, and having pipecolic acid 4-hydroxylase activity; and (C) a polypeptide comprising an amino acid sequence that is not less than 80% identical to the amino acid sequence represented by SEQ ID NO:2, 4, 6, 8, 10, 12, 16, or 18, and having pipecolic acid 4-hydroxylase activity.

[3] The pipecolic acid 4-hydroxylase protein according to [2], which is produced as a recombinant protein by a host having no glycosylation ability.

[4] A method for producing 4-hydroxy amino acid, the method comprising reacting the pipecolic acid 4-hydroxylase protein according to any one of [1] to [3], a cell(s) comprising the protein, a treated product of the cell(s), and/or a culture liquid obtained by culturing the cell(s), with α-amino acid to produce 4-hydroxy amino acid.

[5] The method for producing 4-hydroxy amino acid according to [4], wherein the α-amino acid is represented by the following General Formula (I):

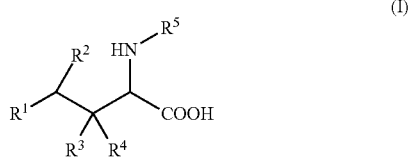

(I)

(wherein each of $R^1$, $R^2$, $R^3$, $R^4$, and $R^5$ represents a hydrogen atom or $C_1$-$C_3$ alkyl, and alternatively $R^2$ may bind to $R^5$ or the nitrogen atom of the amino group to form a ring structure),
and the 4-hydroxy amino acid is represented by the following General Formula (II):

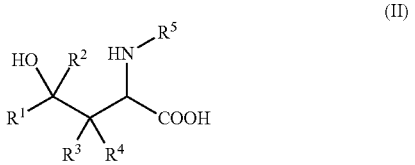

(II)

(wherein each of $R^1$, $R^2$, $R^3$, $R^4$, and $R^5$ represents a hydrogen atom or $C_1$-$C_3$ alkyl, and alternatively $R^2$ may bind to $R^5$ or the nitrogen atom of the amino group to form a ring structure).

[6] The method for producing 4-hydroxy amino acid according to [4], wherein the α-amino acid is pipecolic acid, and 4-hydroxy amino acid is 4-hydroxy-L-pipecolic acid.

[7] The method for producing 4-hydroxy amino acid according to any one of [4] to [6], wherein the cell comprising pipecolic acid 4-hydroxylase is a cell transformed with a DNA encoding pipecolic acid 4-hydroxylase protein.

[8] The method for producing 4-hydroxy amino acid according to [7], wherein the DNA encoding pipecolic acid 4-hydroxylase protein is selected from the group consisting of the following (D), (E), and (F):

(D) a DNA comprising the nucleotide sequence represented by SEQ ID NO:1, 3, 5, 7, 9, 11, 15, or 17;

(E) a DNA comprising the nucleotide sequence represented by SEQ ID NO:1, 3, 5, 7, 9, 11, 15, or 17 except that one or several bases are substituted, deleted, and/or added, and encoding a polypeptide having pipecolic acid 4-hydroxylase activity; and (F) a DNA comprising a nucleotide sequence which hybridizes with the complementary strand of the nucleotide sequence represented by SEQ ID NO:1, 3, 5, 7, 9, 11, 15, or 17 under stringent conditions, and encoding a polypeptide having pipecolic acid 4-hydroxylase activity.

[9] A microorganism transformed with a DNA encoding a pipecolic acid 4-hydroxylase protein selected from the group consisting of the following (D), (E), and (F):

(D) a DNA comprising the nucleotide sequence represented by SEQ ID NO:1, 3, 5, 7, 9, 11, 15, or 17;

(E) a DNA comprising the nucleotide sequence represented by SEQ ID NO:1, 3, 5, 7, 9, 11, 15, or 17 except that one or several bases are substituted, deleted, and/or added, and encoding a polypeptide having pipecolic acid 4-hydroxylase activity; and (F) a DNA comprising a nucleotide sequence which hybridizes with the complementary strand of the nucleotide sequence represented by SEQ ID NO:1, 3, 5, 7, 9, 11, 15, or 17 under stringent conditions, and encoding a polypeptide having pipecolic acid 4-hydroxylase activity.

[10] The microorganism according to [9], which is selected from the group consisting of the genera *Escherichia*, *Bacillus*, *Pseudomonas*, and *Corynebacterium*.

Effect of the Invention

According to the present invention, various 4-hydroxy amino acids can be efficiently produced. In particular, optically active 4-hydroxy amino acids such as (4S)-hydroxy-L-pipecolic acid and (4S)-hydroxy-D-pipecolic acid, which are useful as intermediates of pharmaceuticals, can be efficiently produced at high optical purities.

EMBODIMENTS FOR CARRYING OUT THE INVENTION

Figure 1:
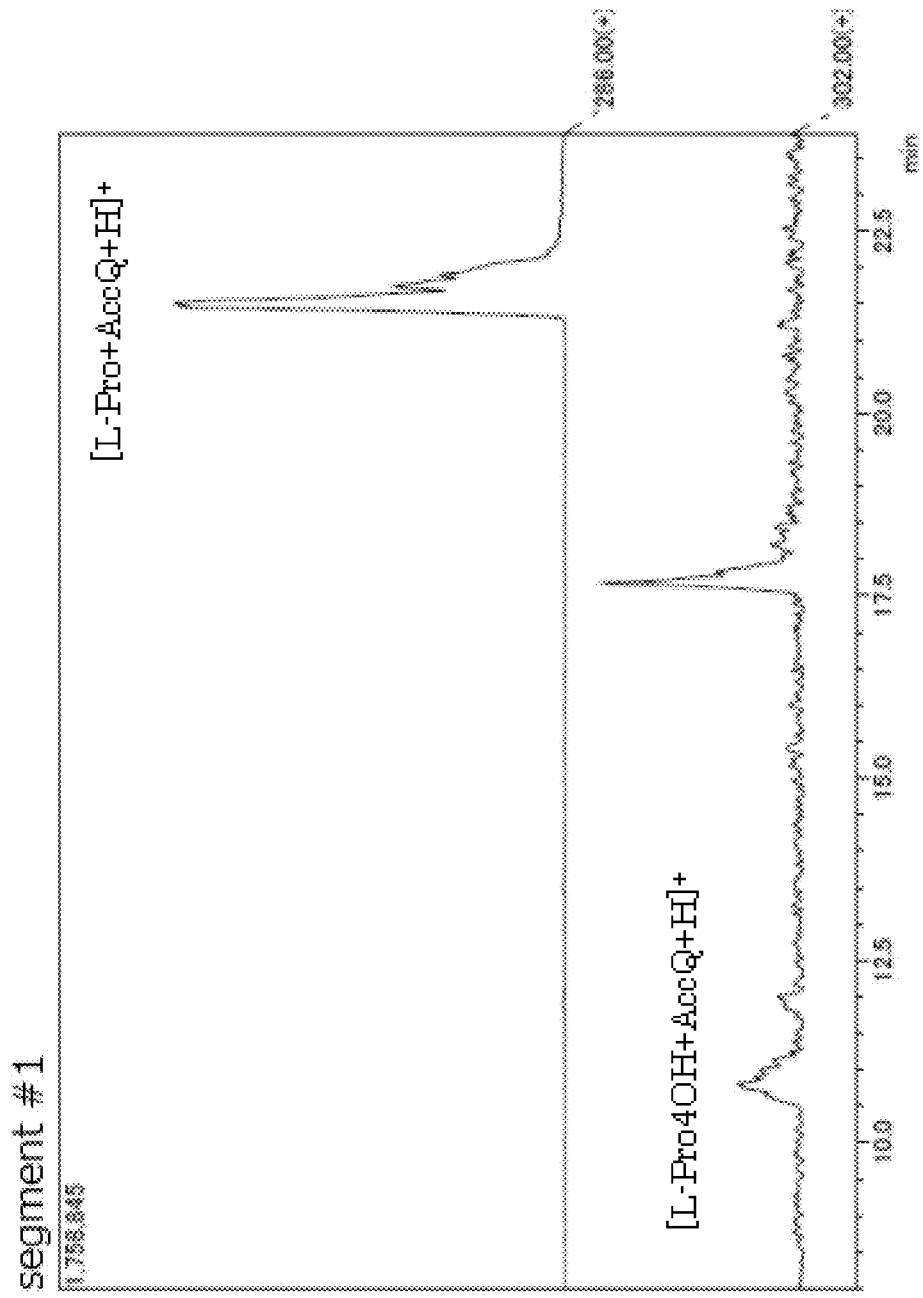
FIG. 1 is a diagram showing the result of LC-MS analysis of a reaction liquid obtained by reacting L-proline with *E. coli* transformed with pFoPA4H.

The present invention is described below in detail.
<Pipecolic Acid 4-Hydroxylase, and Method for Producing 4-Hydroxy Amino Acid Using THE SAME>

The pipecolic acid 4-hydroxylase of the present invention comprises the amino acid sequence of SEQ ID NO:2, 4, 6, 8, 10, 12, 16, or 18, or a homologue sequence thereof having pipecolic acid 4-hydroxylase activity.

The amino acid sequences of SEQ ID NOs:2, 4, 6, 8, 10, and 12 are derived from the *Fusarium oxysporum* c8D strain, *Aspergillus oryzae* RIB40 strain, *Penicillium chrysogenum* Wisconsin 54-1255 strain, *Gibberella zeae* (another name, *Fusarium graminearum*) PH-1 strain, *Colletotrichum gloeosporioides* Nara gc5 strain, and *Aspergillus nidulans* (another name, *Emericella nidulans*) FGSC A4 strain, respectively. These are the amino acid sequences of proteins identified as pipecolic acid 4-hydroxylase in the present invention. The amino acid sequences of SEQ ID NOs:16 and 18 are sequences obtained by analysis of DNAs directly collected from samples of soils in Japan, and are the amino acid sequences of proteins identified as pipecolic acid 4-hydroxylase in the present invention. Although the amino acid sequence of SEQ ID NO:16 shows a homology of 97% to a protein which is derived from *Variovorax paradoxus* EPS and whose function is unknown (GenBank accession No. YP_004156498), there is no report describing its function. Further, although the amino acid sequence of SEQ ID NO:18 shows a homology of 50% to a protein which is derived from *Burkholderia* sp A1 and whose function is unknown (GenBank accession No. WP_029951026), there is no report describing its function.

None of these sequences can be easily assumed to be a hydroxylase for pipecolic acid based only on its sequence information. The present invention identified them as pipecolic acid 4-hydroxylases for the first time.

A plurality of types of pipecolic acid 4-hydroxylases may be used.

In the present description, the pipecolic acid 4-hydroxylase activity means an activity which adds a hydroxyl group to the 4-position carbon atom of L-pipecolic acid in the presence of 2-oxoglutaric acid and iron(II) ions, to produce trans-4-hydroxy-L-pipecolic acid. Such an activity can be confirmed by allowing, as an enzyme, the protein of interest, a cell(s) expressing the protein, or a treated product thereof to act in a reaction system containing L-pipecolic acid as a substrate and 2-oxoglutaric acid and iron(II) ions as cofactors, and then measuring the production of trans-4-hydroxy-L-pipecolic acid as described in the later-mentioned Examples.

Examples of the homologue of the pipecolic acid 4-hydroxylase comprising the amino acid sequence of SEQ ID NO:2, 4, 6, 8, 10, 12, 16, or 18 in the present invention include those comprising the amino acid sequence of SEQ ID NO:2, 4, 6, 8, 10, 12, 16, or 18 except that one or several amino acids are deleted, substituted, and/or added, as long as the homologues have pipecolic acid 4-hydroxylase activity. Here, the term "one or several amino acids" means, for example, 1 to 100, preferably 1 to 50, more preferably 1 to 20, still more preferably 1 to 10, especially preferably 1 to 5 amino acids.

The homologue may be a protein having a sequence that is not less than 80%, preferably not less than 90%, more preferably not less than 95%, identical to the full-length amino acid sequence of SEQ ID NO: 2, 4, 6, 8, 10, 12, 16, or 18 as long as the homologue maintains pipecolic acid 4-hydroxylase activity.

The pipecolic acid 4-hydroxylase that may be used in the present invention can be obtained by purification from the microorganisms described above, or can be obtained by cloning a DNA encoding the pipecolic acid 4-hydroxylase by a known method such as PCR or hybridization, and allowing expression of the pipecolic acid 4-hydroxylase in an appropriate host.

Examples of the DNA encoding pipecolic acid 4-hydroxylase include DNAs comprising the nucleotide sequence represented by SEQ ID NOs:1, 3, 5, 7, 9, 11, 15, or 17.

The DNA encoding pipecolic acid 4-hydroxylase may also be a homologue of a DNA comprising the nucleotide sequence of SEQ ID NO:1, 3, 5, 7, 9, 11, 15, or 17 as long as the DNA encodes a protein having pipecolic acid 4-hydroxylase activity. Examples of such a homologue include those comprising the nucleotide sequence of SEQ ID NO:1, 3, 5, 7, 9, 11, 15, or 17 except that one or several nucleotides are substituted, deleted, and/or added.

Here, the term "one or several nucleotides" means, for example, 1 to 300, preferably 1 to 150, more preferably 1 to 60, still more preferably 1 to 30, especially preferably 1 to 15 nucleotides.

The DNA homologue may be a DNA which hybridizes with the complementary strand of the nucleotide sequence of SEQ ID NO:1, 3, 5, 7, 9, 11, 15, or 17 under stringent conditions, as long as the DNA homologue encodes a protein having pipecolic acid 4-hydroxylase activity. Examples of the "stringent conditions" herein include conditions in which washing is carried out in the presence of 0.1×SSC (saline-sodium citrate) and 0.1% SDS (sodium dodecyl sulfate) at 60° C.

Those skilled in the art can obtain such a DNA homologue by appropriately introducing a substitution, deletion, insertion, and/or addition mutation(s) into the DNA of SEQ ID NO:1, 3, 5, 7, 9, 11, 15, or 17 by site-directed mutagenesis (Nucleic Acids Res. 10, pp. 6487 (1982); Methods in Enzymol. 100, pp. 448 (1983); Molecular Cloning, PCR A Practical Approach IRL Press pp. 200 (1991)) or the like.

The amino acid sequence of SEQ ID NO:2, 4, 6, 8, 10, 12, 16, or 18 or a part thereof, or the nucleotide sequence represented by SEQ ID NO:1, 3, 5, 7, 9, 11, 15, or 17 or a part thereof may be subjected to homology search against a database provided by, for example, DNA Databank of JAPAN (DDBJ), to obtain amino acid information for the pipecolic acid 4-hydroxylase activity, or nucleotide sequence information of a DNA encoding it.

In the method for producing 4-hydroxy amino acid of the present invention, pipecolic acid 4-hydroxylase may be directly used in the reaction. However, it is preferred to use cells containing pipecolic acid 4-hydroxylase, a treated product of the cells, or a culture liquid obtained by culturing the cells.

The cells containing pipecolic acid 4-hydroxylase may be cells of a microorganism intrinsically having pipecolic acid 4-hydroxylase. However, it is preferred to use cells transformed with a gene encoding pipecolic acid 4-hydroxylase.

Examples of the treated product of the cells containing pipecolic acid 4-hydroxylase include treated cell products such as those obtained by treatment with an organic solvent such as acetone, dimethylsulfoxide (DMSO), or toluene, or with a surfactant, those obtained by freeze-drying, and those obtained by physical or enzymatic destruction; enzyme fractions of the cells obtained as a crude product or a purified product; and products prepared by immobilizing these on a carrier such as polyacrylamide gel and carrageenan gel.

By inserting the thus isolated DNA encoding pipecolic acid 4-hydroxylase into a known expression vector in a manner which allows expression of the pipecolic acid 4-hydroxylase, a pipecolic acid 4-hydroxylase-expressing vector is provided. By transforming host cells with this expression vector, a transformant to which a DNA encoding pipecolic acid 4-hydroxylase is introduced can be obtained. The transformant can also be obtained by incorporating a DNA encoding pipecolic acid 4-hydroxylase into the chromosomal DNA of a host by a method such as homologous recombination in a manner which allows expression of the pipecolic acid 4-hydroxylase.

Specific examples of the method for preparing the transformant include a method in which a DNA encoding pipecolic acid 4-hydroxylase is introduced into a plasmid vector, phage vector, or virus vector which can be stably present in a host cell such as a microorganism cell, and the constructed expression vector is introduced into the host cell, or the DNA is directly into the host genome, followed by allowing transcription and translation of the genetic information. In this process, an appropriate promoter is preferably linked 5'-upstream of the DNA, and, in addition, a terminator is preferably linked 3'-downstream of the DNA. Such a promoter and a terminator are not limited as long as they are a promoter and a terminator known to function in the cell used as a host. For example, "Fundamental Microbiology 8: Genetic Engineering, KYORITSU SHUPPAN CO., LTD." describes details of vectors, promoters, and terminators that can be used in host microorganisms.

The host microorganism to be transformed for expression of pipecolic acid 4-hydroxylase is not limited as long as the host itself does not adversely affect the reaction of α-amino acid, and specific examples of the host microorganism include the following microorganisms:

Bacteria belonging to the genera *Escherichia, Bacillus, Pseudomonas, Serratia, Brevibacterium, Corynebacterium, Streptococcus, Lactobacillus*, and the like whose host vector systems have been established.

Actinomycetes belonging to the genera *Rhodococcus, Streptomyces*, and the like whose host vector systems have been established.

Yeasts belonging to the genera *Saccharomyces, Kluyveromyces, Schizosaccharomyces, Zygosaccharomyces, Yarrowia, Trichosporon, Rhodosporidium, Hansenula, Pichia, Candida*, and the like whose host vector systems have been established.

Fungi belonging to the genera *Neurospora, Aspergillus, Cephalosporium, Trichoderma*, and the like whose host vector systems have been established.

The procedure for construction of the transformant, the method for construction of a recombinant vector suitable for the host, and the method for culturing the host can be carried out according to techniques commonly used in the fields of molecular biology, bioengineering, and genetic engineering (for example, methods described in Molecular Cloning).

The following are specific examples of preferred host microorganisms, and preferred methods of transformation, vectors, promoters, terminators, and the like for the microorganisms. The present invention is not limited to these examples.

For the genus *Escherichia*, especially *Escherichia coli*, examples of the plasmid vector include pBR and pUC plasmids, and examples of the promoter include promoters derived from lac (β-galactosidase), trp (tryptophan operon), tac, trc (fusion of lac and trp), and λ phage PL and PR. Examples of the terminator include terminators derived from trpA, phages, and rrnB ribosomal RNA.

For the genus *Bacillus*, examples of the vector include pUB110 plasmids and pC194 plasmids. Integration into the chromosome is also possible. Examples of the promoter and the terminator include those of genes of enzymes such as alkaline protease, neutral protease, and α-amylase.

For the genus *Pseudomonas*, examples of the vector include common host vector systems established in *Pseudomonas putida, Pseudomonas cepacia*, and the like; and a wide-host-range vector (containing genes required for autonomous replication derived from RSF1010 and the like) pKT240, which is based on a plasmid involved in degradation of toluene compounds, TOL plasmid (Gene, 26, 273-82 (1983)).

For the genus *Brevibacterium*, especially *Brevibacterium lactofermentum*, examples of the vector include plasmid vectors such as pAJ43 (Gene 39, 281 (1985)). Examples of the promoter and the terminator include promoters and terminators used in *E. coli*.

For the genus *Corynebacterium*, especially *Corynebacterium glutamicum*, examples of the vector include plasmid vectors such as pCS11 (JP 57-183799 A) and pCB101 (Mol. Gen. Genet. 196, 175 (1984)).

For the genus *Saccharomyces*, especially *Saccharomyces cerevisiae*, examples of the vector include YRp, YEp, YCp, and YIp plasmids. Examples of promoters and terminators which may be used include those of the genes of enzymes such as alcohol dehydrogenase, glyceraldehyde-3-phosphate dehydrogenase, acid phosphatase, β-galactosidase, phosphoglycerate kinase, and enolase.

For the genus *Schizosaccharomyces*, examples of the vector include the plasmid vector derived from *Schizosaccharomyces pombe* described in Mol. Cell. Biol. 6, 80 (1986). In particular, pAUR224 is commercially available from Takara Shuzo Co., Ltd., and can be easily used.

In terms of the genus *Aspergillus, Aspergillus niger, Aspergillus oryzae*, and the like are the best-studied species among fungi. Plasmids, and integration into the chromosome are applicable to these species, and promoters derived from extracellular protease and amylase can be used (Trends in Biotechnology 7, 283-287 (1989)).

Among the microorganisms described above, examples of especially preferred microorganisms include microorganisms belonging to the genera *Escherichia, Bacillus, Pseudomonas*, and *Corynebacterium* having no glycosylation ability.

Host-vector systems other than the above-described systems have also been established for various microorganisms, and those systems may be used as appropriate.

Various host-vector systems have been established for plants and animals besides microorganisms. In particular, systems for allowing expression of a large amount of foreign protein in an animal such as an insect including silkworm (Nature 315, 592-594 (1985)), or in a plant such as rapeseed, maize, or potato; and systems using cell-free protein synthesis systems such as *E. coli* cell-free extracts and wheat germs; have been established, and may be preferably used.

By reacting pipecolic acid 4-hydroxylase, cells containing the enzyme, a treated product of the cells, or a culture liquid of the cells, with the reaction substrate α-amino acid in the presence of 2-oxoglutaric acid and iron(II) ions, 4-hydroxy amino acid is produced.

Here, the α-amino acid as the reaction substrate is not limited as long as it has a hydrogen atom which can be substituted with a hydroxyl group at 4-position. Examples of the α-amino acid include compounds represented by the following General Formula (I). Examples of the 4-hydroxy amino acid include compounds represented by the following General Formula (II). Each of the α-amino acid and the 4-hydroxy amino acid is preferably an L-isomer or a D-isomer, but may also be a racemic mixture.

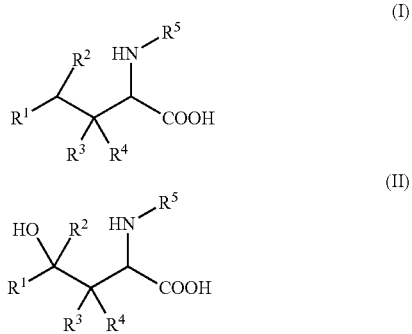

In General Formulae (I) and (II), each of $R^1$, $R^2$, and $R^5$ represents a hydrogen atom or $C_1$-$C_3$ alkyl, and each of $R^3$ and $R^4$ represents a hydrogen atom, $C_1$-$C_3$ alkyl, or hydroxyl. Alternatively, $R^2$ may bind to $R^5$ or the nitrogen atom of the amino group to form a ring structure.

Specific examples of the type of the α-amino acid include valine, leucine, isoleucine, proline (in which $R^2$ is bound to the nitrogen atom of the amino group to form a five-membered ring), α-aminobutyric acid, norvaline, norleucine, pipecolic acid (in which $R^2$ is bound to $R^5$ to form a six-membered ring), 3-hydroxyproline, 3-hydroxypipecolic acid, and 5-hydroxypipecolic acid. The α-amino acid is especially preferably pipecolic acid.

The reaction is carried out in an aqueous medium containing: the α-amino acid; 2-oxoglutaric acid; iron(II) ions; and the pipecolic acid 4-hydroxylase or the cells containing it, the treated product of the cells, or the culture product of the cells; or carried out in a mixture of the aqueous medium and an organic solvent.

Examples of the aqueous medium include water and buffers. Here, the buffers are not limited as long as the activity of the pipecolic acid 4-hydroxylase is not inhibited thereby. Examples of the buffers include phosphate buffer and MES (2-Morpholinoethanesulfonic acid) buffer. Examples of the organic solvent include those in which the reaction substrate is highly soluble, such as methanol, ethanol, 1-propanol, 2-propanol, 1-butanol, tort-butanol, acetone, and dimethyl sulfoxide. Other examples of the organic solvent include ethyl acetate, butyl acetate, toluene, chloroform, and n-hexane, which are effective for removal of reaction by-products, and the like.

The reaction substrate, α-amino acid, is usually used at a substrate concentration within the range of 0.01% w/v to 90% w/v, preferably 0.1% w/v to 30% w/v. The reaction substrate may be added at once when the reaction is started, but is preferably added continuously or intermittently from the viewpoint of reducing the influence of substrate inhibition of the enzyme, if any, and increasing the concentration of the product accumulated.

The number of moles of the 2-oxoglutaric acid required for the reaction is normally equivalent to, or higher than, that of the substrate, preferably equivalent to, or up to 1.2-fold higher than, that of the substrate. The 2-oxoglutaric acid may be added at once when the reaction is started, but is preferably added continuously or intermittently from the viewpoint of reducing the inhibitory action on the enzyme, if any, and increasing the concentration of the product accumulated. Alternatively, an inexpensive compound that can be metabolized by the host, such as glucose or L-glutamic acid, may be added instead of 2-oxoglutaric acid to allow metabolism of the compound by the host, and 2-oxoglutaric acid produced during this process may be used for the reaction.

The iron(II) ions required for the reaction are used within the range of usually 0.01 mmol/L to 100 mmol/L, preferably 0.1 mmol/L to 10 mmol/L. The iron(II) ions are usually added at once when the reaction is started. Further addition of iron(II) ions is also effective in cases where the iron(II) ions decrease during the reaction due to oxidation into iron(III) ions or formation of a precipitate. In cases where a sufficient amount of iron(II) ions are already contained in the pipecolic acid 4-hydroxylase, the cells containing the enzyme, the treated product of the cells, or the culture liquid of the cells, the addition of iron(II) ions is not required.

The reaction is carried out at a reaction temperature of usually 4° C. to 60° C., preferably 10° C. to 45° C., at a pH of usually 3 to 11, preferably 5 to 8. The reaction time is usually about 1 hour to about 72 hours.

The amount of the cells and/or the treated cell product to be added to the reaction liquid is as follows. In cases of addition of the cells, the cells are added to the reaction liquid such that the cell concentration is usually about 0.1% w/v to about 50% w/v, preferably 1% w/v to 20% w/v, in terms of the wet cell weight. In cases of using the treated cell product, the specific activity of the enzyme in the treated cell product is determined, and the treated cell product is added such that the cell concentration described above is achieved.

After completion of the reaction, the 4-hydroxy amino acid produced by the method of the present invention may be subjected to separation of microbial cells, proteins, and/or the like in the reaction liquid by centrifugation, membrane treatment, and/or the like, and then to purification by an appropriate combination of, for example, extraction with an organic solvent such as 1-butanol or tert-butanol, distillation, column chromatography using an ion-exchange resin, silica gel, or the like, crystallization at the isoelectric point, and/or crystallization with monohydrochloride, dihydrochloride, calcium salt, or the like.

EXAMPLES

The present invention is described below in more detail by way of Examples, but the present invention is not limited to the Examples.

Example 1

<Construction of Plasmid Expressing Pipecolic Acid 4-Hydroxylase Gene>
(1) Gene Cloning Based on a gene sequence encoding a hypothetical protein FOXB 08233 derived from *Fusarium oxysporum* Fo5176, primers BOF1 and BOR1 for amplification of full-length homologous genes for the hypothetical protein FOXB_08233 were designed and synthesized. The nucleotide sequences of the primers are shown in SEQ ID NOs:13 and 14.

*Fusarium oxysporum* c8D was cultured overnight in a potato dextrose liquid medium (manufactured by Becton, Dickinson and Company, Japan). From the microbial cells obtained, chromosomal DNA was prepared using a DNeasy Blood & Tissue Kit (manufactured by QIAGEN).

Using the thus prepared chromosomal DNA derived from each microbial strain as a template, and the oligonucleotides of SEQ ID NOs:13 and 14 as primers, polymerase chain reaction (PCR) was carried out to amplify a DNA fragment of about 1 kbp. The PCR was carried out using Tks Gflex DNA polymerase (manufactured by Takara Bio Inc.) according to the conditions described in the manufacturer's instruction. The temperature program was as follows: the temperature was kept at 95° C. for 1 minute, and then 35 cycles of (98° C., 10 seconds; 56.5° C., 15 seconds; and 68° C., 40 seconds) were carried out, followed by keeping the temperature at 72° C. for 3 minutes to complete the reaction. The result of analysis of the DNA sequence obtained is shown in SEQ ID NO:1, and the amino acid sequence encoded by this DNA sequence is shown in SEQ ID NO:2.
(2) Preparation of Expression Plasmid The DNA fragment obtained in (1) was digested with restriction enzymes BamHI and HindIII, and introduced into a plasmid vector pQE80L (manufactured by QIAGEN) digested with the restriction enzymes BamHI and HindIII, using a Ligation-Convenience Kit (manufactured by Nippon Gene Co., Ltd.). The plasmid obtained is hereinafter referred to as pFoPA4H. In addition, the DNA sequences of SEQ ID NOs:3, 5, 7, 9, and 11 were synthesized by DNA2.0, Inc., and inserted into an expression plasmid pJexpress411 by the same manufacturer. The plasmids obtained are hereinafter referred to as pAoPA4H, pPcPA4H, pGzPA4H, pCgPA4H, and pEnPA4H.

Example 2

<Evaluation of Pipecolic Acid 4-Hydroxylase Activity>

The six kinds of plasmids obtained in Example 1, pFoPA4H, pAoPA4H, pPcPA4H, pGzPA4H, pCgPA4H, and pEnPA4H, were used for transformation of *E. coli* (*Escherichia coli*) Rosetta 2 (DE3) (manufactured by Merck Millipore Corporation) according to an ordinary method. Each recombinant *E. coli* obtained was cultured with shaking at 30° C. using liquid LB medium supplemented with 50 mg/L kanamycin, 15 mg/L chloramphenicol, and 1 mmol/L IPTG (isopropyl β-D-1-thiogalactopyranoside) for 20 hours, and the cultured bacterial cells were collected.

The bacterial cells obtained were subjected to reaction at 20° C. at pH 6 for 21 hours in 50 mmol/L IVIES (2-morpholinoethanesulfonic acid) buffer supplemented with 15 mmol/L 2-oxoglutaric acid, 5 mmol/L ascorbic acid, 5 mmol/L tris(2-carboxyethyl)phosphine hydrochloride, 0.5 mmol/L $FeSO_4 \cdot 7H_2O$, 3 mmol/L citric acid, and 10 mmol/L each substrate compound.

The reaction liquids after the reaction were analyzed by high-performance liquid chromatography (HPLC) under the following conditions.
Column: CHIRALPAK AD-3 (4.6×250 mm, manufactured by Daicel Corporation)
Eluent: hexane:ethanol:trifluoroacetic acid=95:5:0.1
Flow rate: 0.8 ml/min.
Temperature: 30° C.
Detection: UV 210 nm Example 3

<Identification of Reaction Products>

Each reaction liquid obtained in Example 2 was derivatized using the Waters AccQ•Tag method, and subjected to separation analysis using a high-performance liquid chromatograph-mass spectrometer (LC-MS) under the following conditions to measure amino acid reaction products.
Column: XBridge C18 5 μm (2.1×150 mm, manufactured by Waters Corporation)
Fluent A: ammonium acetate (10 mmol/L, pH 5)
Eluent B: methanol (0 to 0.5 min. (0%→1%), 0.5 to 18 min. (1%→5%), 18 to 19 min. (5%→9%), 19 to 29.5 min. (9%→17%), 29.5 to 40 min. (17%→60%), 40 to 43 min. (60%))
Flow rate: 0.3 ml/min.
Temperature: 30° C.
Detection: mass spectrometer For the reaction liquids obtained using the six kinds of *E. coli*, substrate amino acids for which appearance of a new peak was found in the LC-MS analysis are shown in Table 1. Since the molecular weights of these new reaction products were found to be higher by 16 compared to the molecular weights of their substrates, it is thought that all of the new reaction products are compounds produced by addition of an oxygen atom to their substrates.

TABLE 1

| Plasmid | Substrate amino acid (the amount of increase in the molecular weight of the reaction product) |
|---|---|
| pFoPA4H | L-pipecolic acid (16), L-proline (16), L-leucine (16), D-norleucine (16) |
| pAoPA4H | L-pipecolic acid (16), L-proline (16), L-leucine (16), D-norleucine (16) |
| pPcPA4H | L-pipecolic acid (16), L-leucine (16) |
| pGzPA4H | L-pipecolic acid (16), L-leucine (16) |
| pCgPA4H | L-pipecolic acid (16), L-leucine (16) |
| pEnPA4H | L-pipecolic acid (16), D-pipecolic acid (16), L-proline (16), D-proline (16), L-leucine (16), L-valine (16), D-valine (16), L-norleucine (16), D-norleucine (16), (S)-2-Aminobutyric acid, L-norvaline (16) |

(1) The result of LC-MS analysis of the reaction liquid containing *E. coli* transformed with pFoPA4H and L-proline is shown in FIG. 1. Since the peak of the reaction product showed the same retention time as that of a standard substance for trans-4-hydroxy-L-proline, the reaction product was assumed to be trans-4-hydroxy-L- proline. The same result was obtained in the cases where E. coli transformed with pAoPA4H or pEnPA4H was used.

Figure 2:
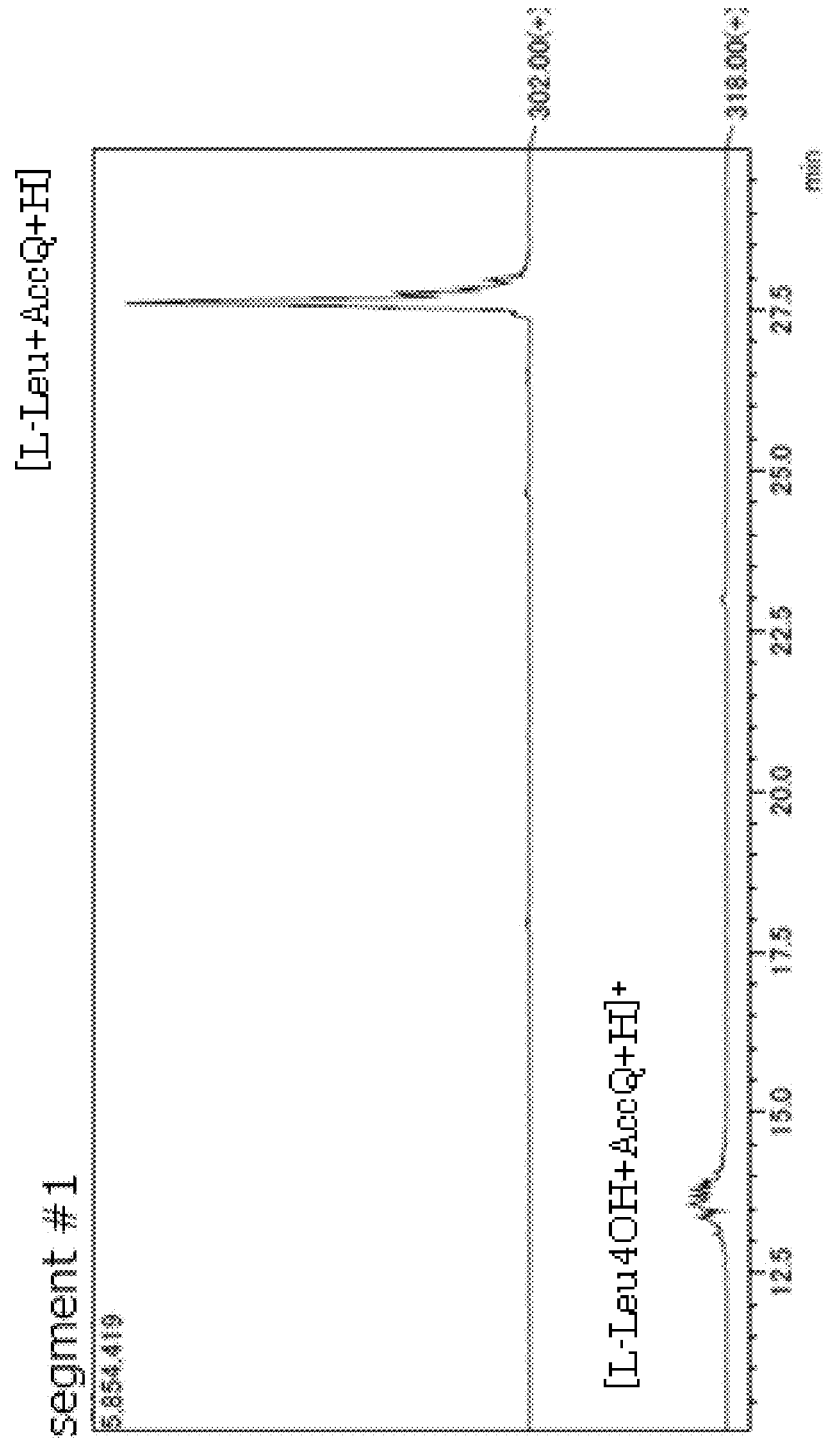
FIG. 2 is a diagram showing the result of LC-MS analysis of a reaction liquid obtained by reacting L-leucine with *E. coli* transformed with pFoPA4H.

(2) The result of LC-MS analysis of the reaction liquid containing E. coli transformed with pFoPA4H and L-leucine are shown in FIG. 2. Since the peak of the reaction product showed the same retention time as that of a standard substance for trans-4-hydroxy-L-leucine, the reaction product was assumed to be trans-4-hydroxy-L-leucine. The same result was obtained in the cases where E. coli transformed with pAoPA4H, pPcPA4H, pGzPA4H, pCgPA4H, or pEnPA4H was used.

(3) A reaction product obtained by reacting L-pipecolic acid with E. coli transformed with pFoPA4H was collected by high-performance liquid chromatography (HPLC) under the following conditions.

Column: TSKgel Amide80 (7.8×300 mm, manufactured by Tosoh Corporation)
Eluent: ammonium acetate (10 mmol/L, pH 5):acetonitrile=15:85
Flow rate: 2.3 ml/min.
Temperature: 40° C.
Detection: UV 210 nm The eluate containing the reaction product was collected, and dried under reduced pressure using a centrifugal evaporator. The resulting residue was suspended in heavy water, and subjected to measurement of the magnetic resonance spectrum.

Figure 6:
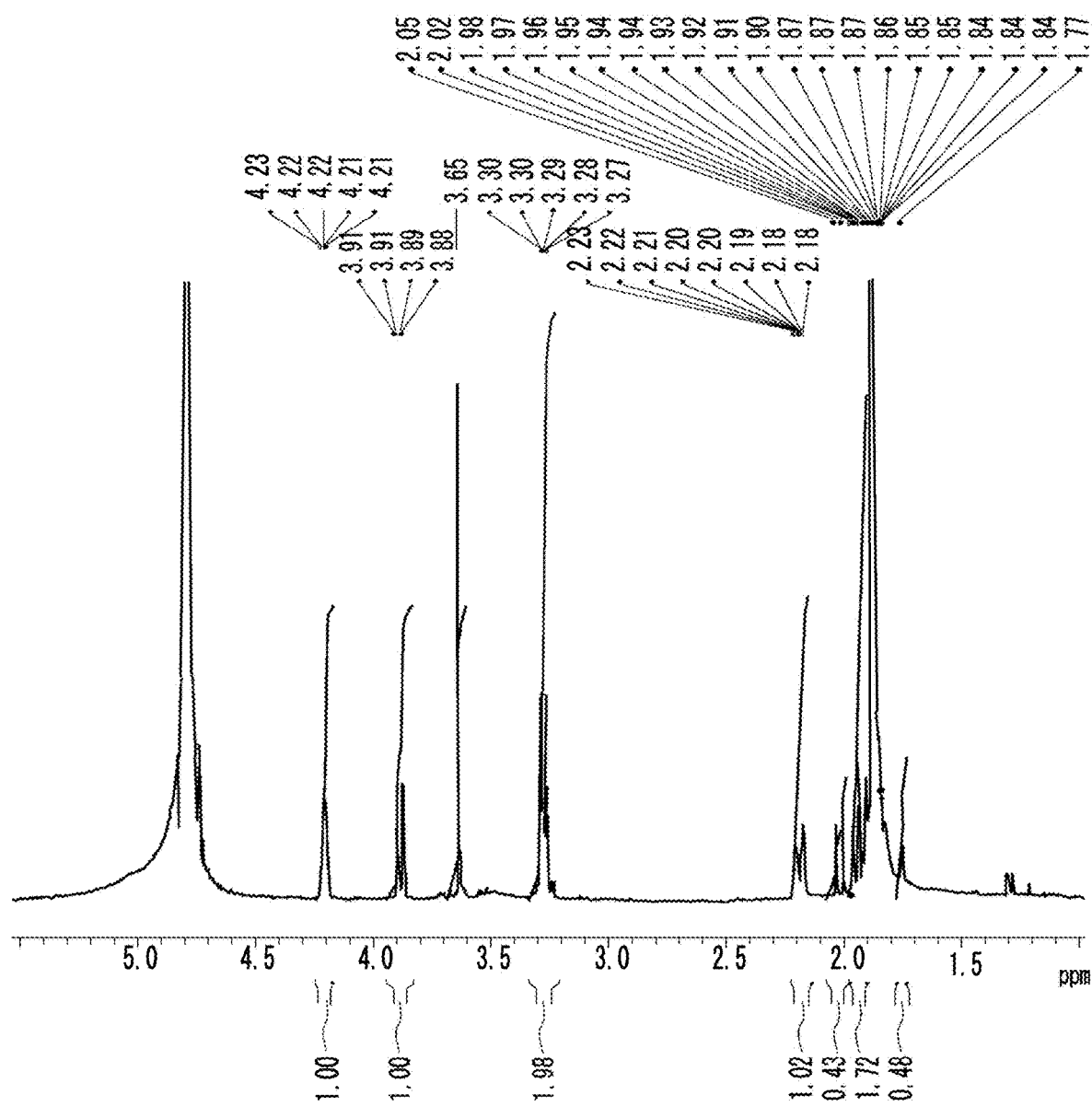
FIG. 6 is a diagram showing the result of $^1$H-NMR analysis of a reaction product obtained by reacting L-pipecolic acid with *E. coli* transformed with pFoPA4H (halftone image).
Figure 7:
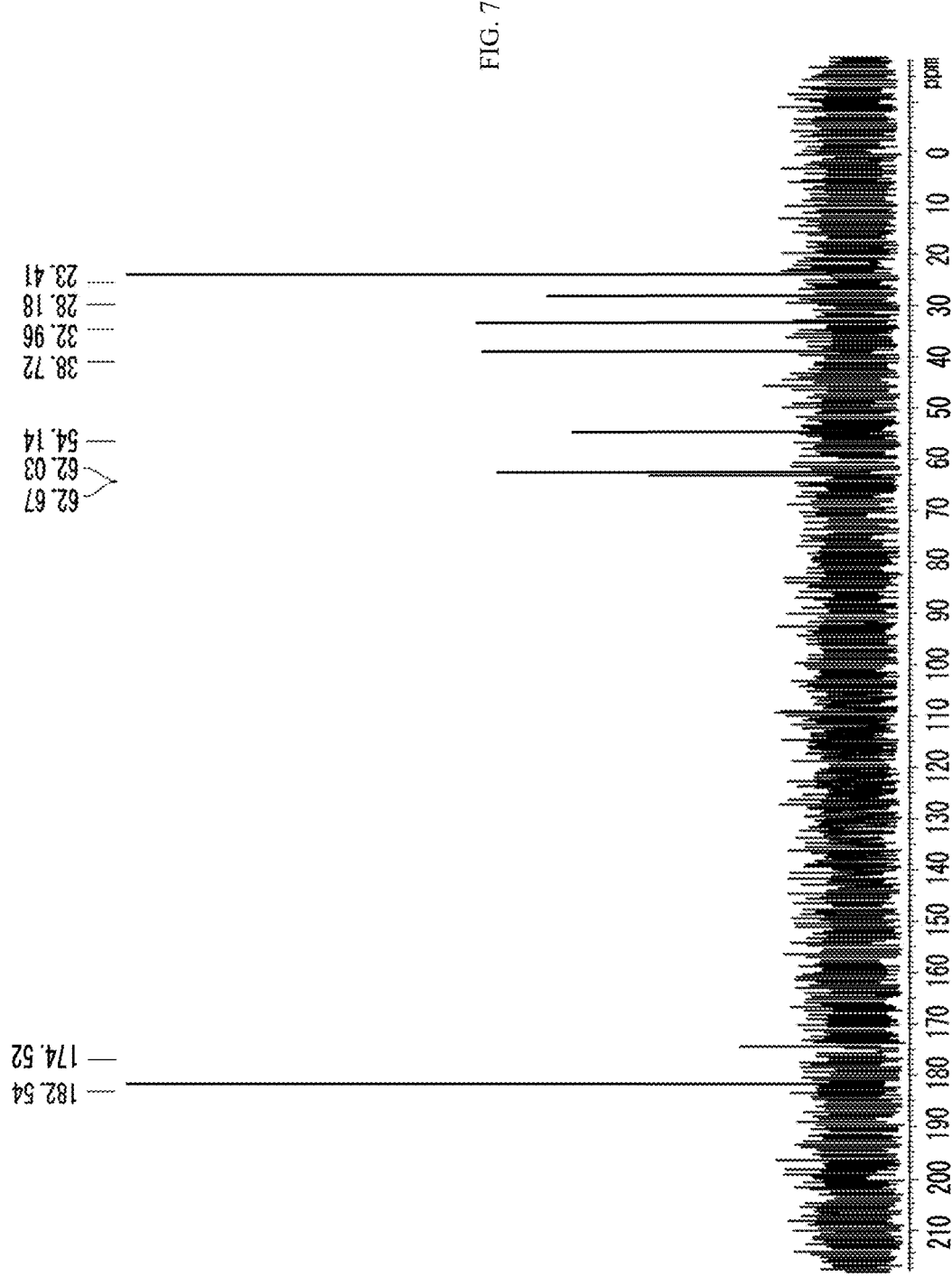
FIG. 7 is a diagram showing the result of $^{13}$C-NMR analysis of a reaction product obtained by reacting L-pipecolic acid with *E. coli* transformed with pFoPA4H (halftone image).
Figure 8:
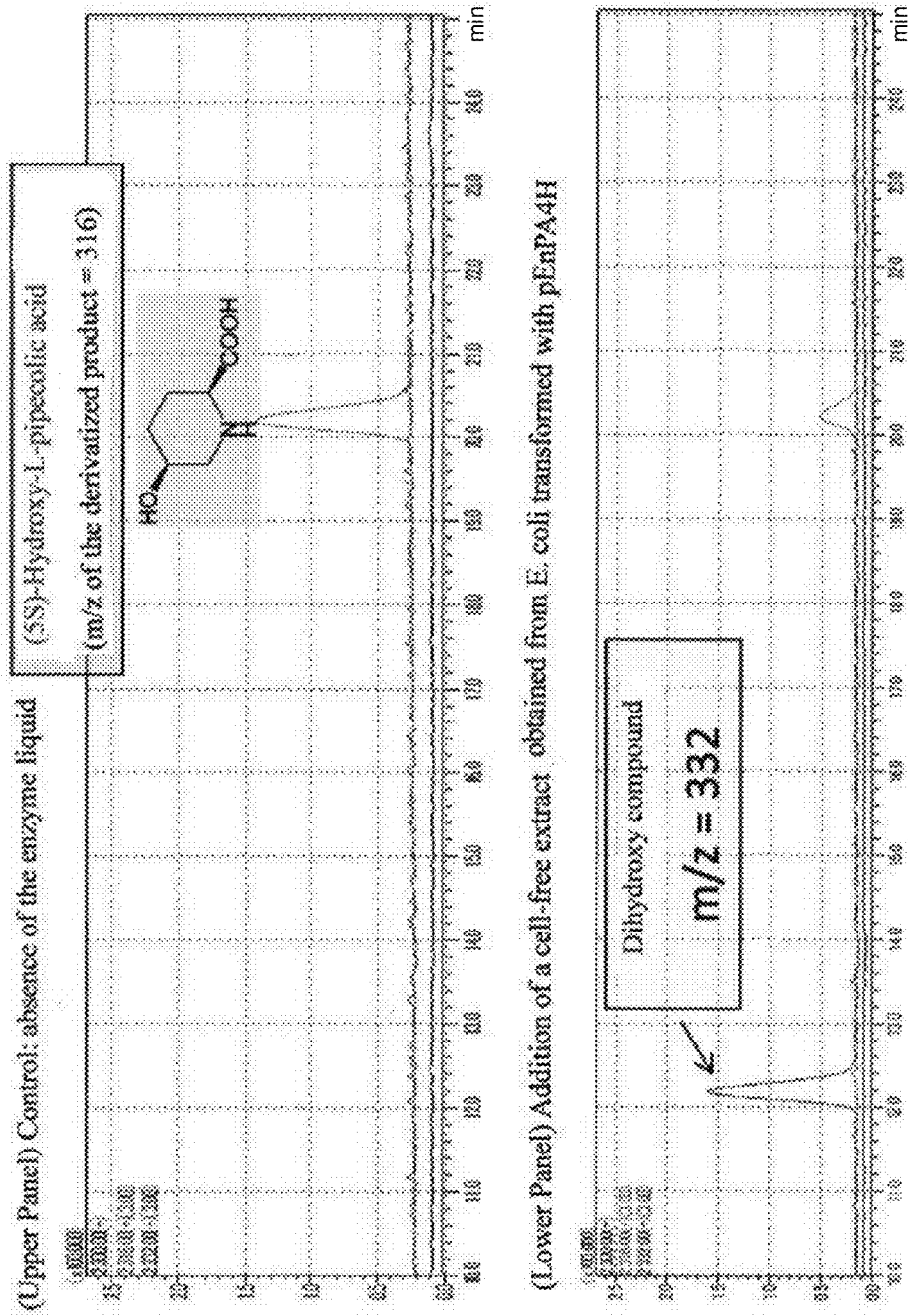
FIG. 8 is a diagram showing the result of LC-MS analysis of a reaction liquid obtained by reacting (5S)-hydroxy-L-pipecolic acid with a cell-free extract obtained from *E. coli* transformed with pEnPA4H.
Figure 9:
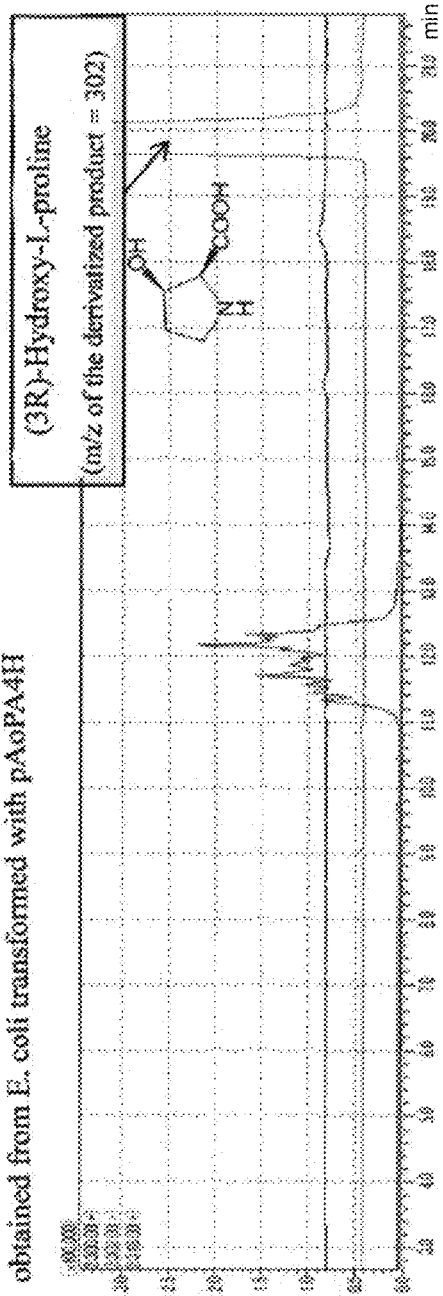
FIG. 9 is a diagram showing the result of LC-MS analysis of a reaction liquid obtained by reacting (3R)-hydroxy-L-proline with a cell-free extract obtained from *E. coli* transformed with pAoPA4H (upper) and with a cell-free extract obtained from *E. coli* transformed with pEnPA4H (lower), respectively.
Figure 9:
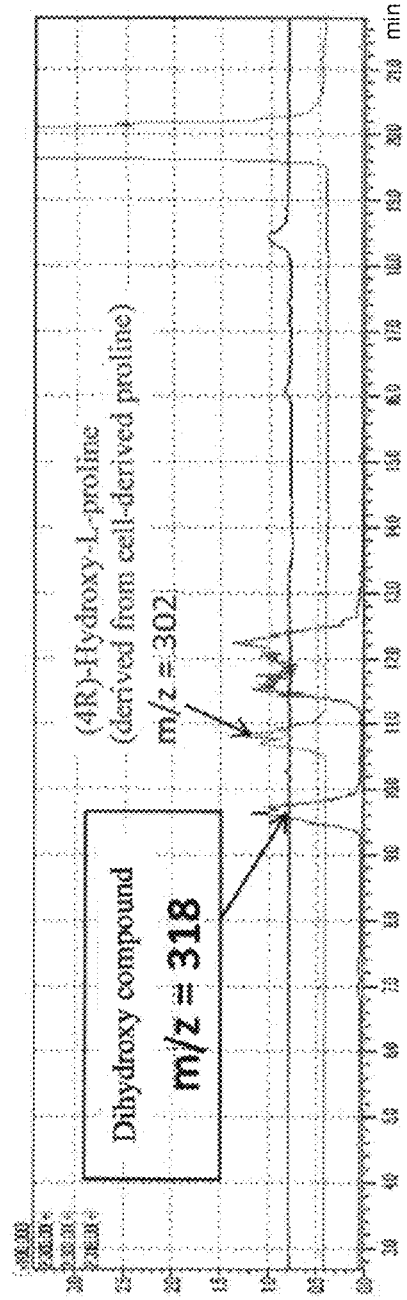

Based on the chemical shift values obtained as a result of $^1$H-NMR (FIG. 6) and $^{13}$C-NMR (FIG. 7), the correlation obtained as a result of HH-COSY and CH-HMQC analyses, and information from a literature (Molnar, T. et al., 2008, Bioorg. Med. Chem. Lett., 18, 6290), the reaction product was identified as trans-4-hydroxy-L-pipecolic acid.

Figure 3:
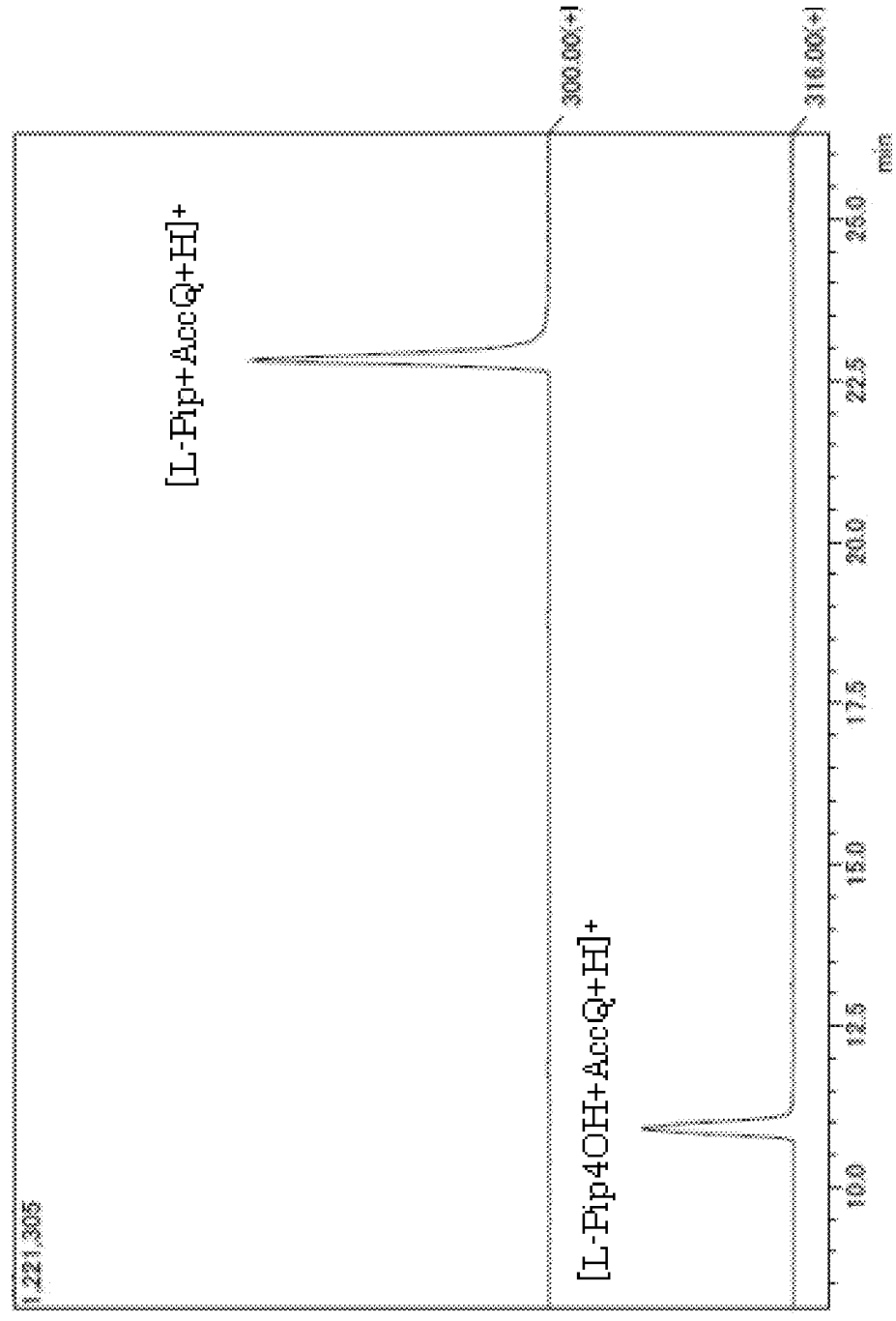
FIG. 3 is a diagram showing the result of LC-MS analysis of a reaction liquid obtained by reacting L-pipecolic acid with *E. coli* transformed with pFoPA4H.

The result of LC-MS analysis of the reaction liquid containing E. coli transformed with pFoPA4H and L-pipecolic acid is shown in FIG. 3. Elution of the peak of the reaction product, trans-4-hydroxy-L-pipecolic acid, occurred at 10.9 minutes. The same result was obtained in the cases where E. coli transformed with pAoPA4H, pPcPA4H, pGzPA4H, pCgPA4H, or pEnPA4H was used.

Figure 4:
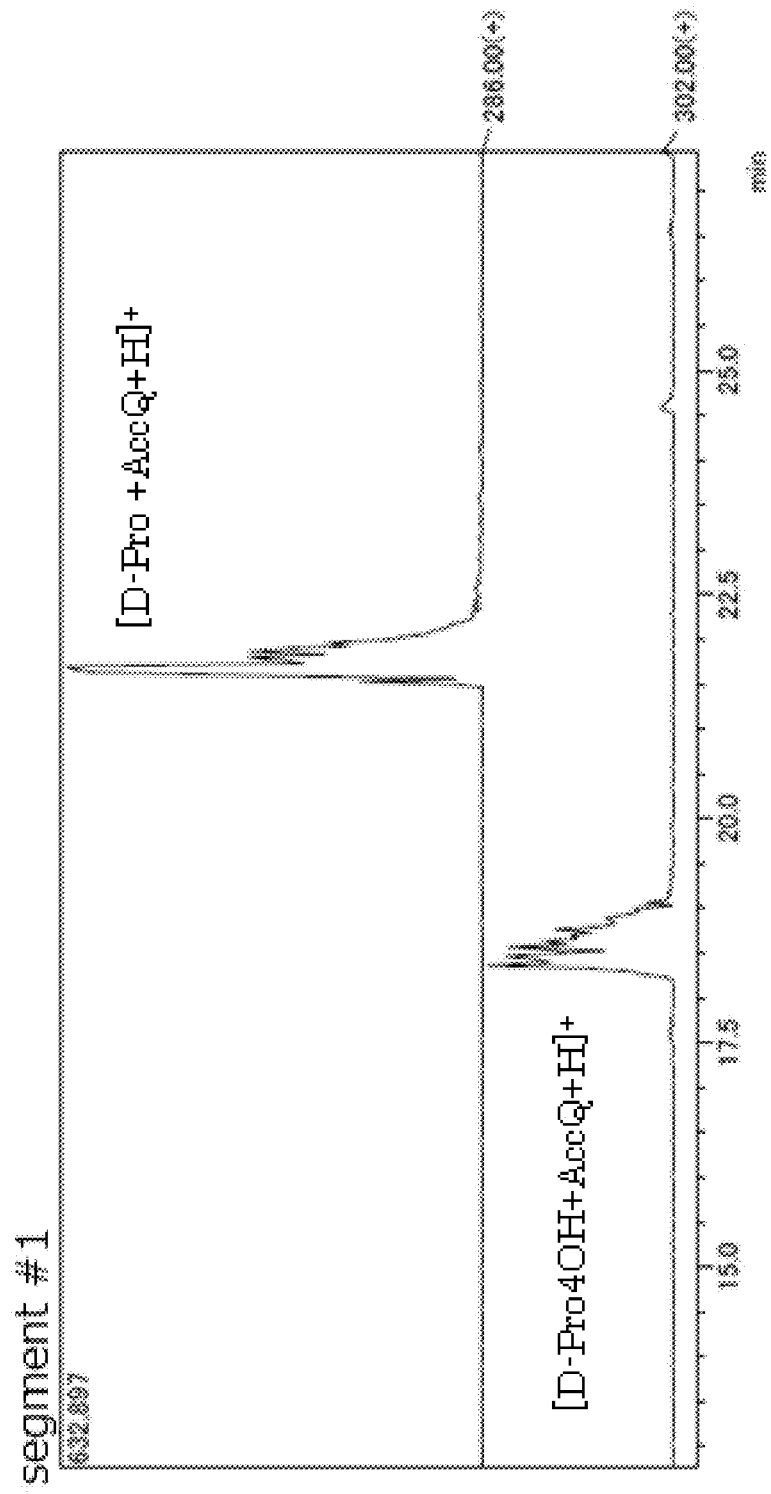
FIG. 4 is a diagram showing the result of LC-MS analysis of a reaction liquid obtained by reacting D-proline with *E. coli* transformed with pEnPA4H.

(4) The result of LC-MS analysis of the reaction liquid containing E. coli transformed with pEnPA4H and D-proline is shown in FIG. 4. Since the peak of the reaction product showed the same retention time as that of a standard substance for cis-4-hydroxy-D-proline, the reaction product was assumed to be cis-4-hydroxy-D-proline.

Figure 5:
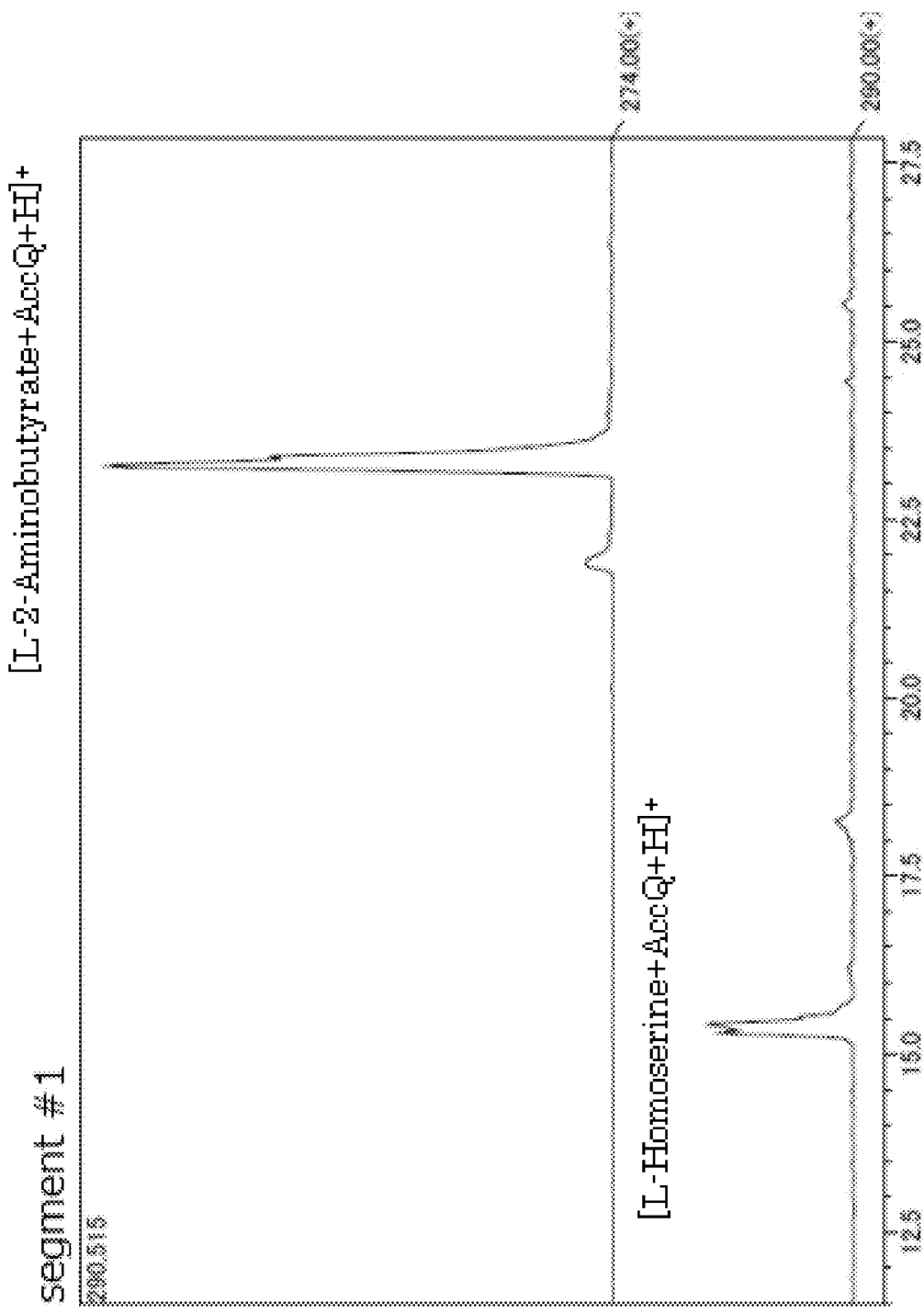
FIG. 5 is a diagram showing the result of LC-MS analysis of a reaction liquid obtained by reacting (S)-2-aminobutyric acid with *E. coli* transformed with pEnPA4H.

(5) The result of LC-MS analysis of the reaction liquid containing E. coli transformed with pEnPA4H and (S)-2-aminobutyric acid is shown in FIG. 5. Since the peak of the reaction product showed the same retention time as that of a standard substance for L-homoserine, the reaction product was assumed to be L-homoserine.

Example 4

<Evaluation of Activity of Pipecolic Acid 4-Hydroxylase for Hydroxylation to Hydroxy Amino Acid>

Using cell-free extracts obtained from the cells obtained in Example 2, reaction was carried out at 20° C. at pH 6 for 21 hours in 50 mmol/L MES buffer supplemented with 15 mmol/L 2-oxoglutaric acid, 5 mmol/L ascorbic acid, 5 mmol/L tris(2-carboxyethyl)phosphine hydrochloride, 0.5 mmol/L FeSO$_4$.7H$_2$O, 3 mmol/L citric acid, and 10 mmol/L each substrate compound. The reaction liquids after the reaction were analyzed by high-performance liquid chromatography (HPLC) under the conditions described in Example 2.

For reaction liquids using two kinds of cell-free extracts, substrate hydroxy amino acids for which appearance of a new peak was found in the LC-MS analysis are shown in Table 2. Since the molecular weights of these new reaction products were found to be higher by 16 compared to the molecular weights of their substrates, it is thought that all of the new reaction products are dihydroxy amino acids produced by addition of an oxygen atom to hydroxy amino acids.

TABLE 2

| Plasmid | Substrate amino acid (the amount of increase in the molecular weight of the reaction product) |
|---|---|
| pFoPA4H | (5S)-hydroxy-L-pipecolic acid (16) |
| pAoPA4H | (5S)-hydroxy-L-pipecolic acid (16) |
| pPcPA4H | (5S)-hydroxy-L-pipecolic acid (16) |
| pGzPA4H | (5S)-hydroxy-L-pipecolic acid (16) |
| pCgPA4H | (5S)-hydroxy-L-pipecolic acid (16) |
| pEnPA4H | (5S)-hydroxy-L-pipecolic acid (16), (3R)-hydroxy-L-proline (16) |

Example 5

<Construction of Plasmids Expressing Pipecolic Acid 4-Hydroxylase Gene>

From results of sequence analysis of DNA directly collected from soil samples, SEQ ID NOs:15 and 17, which could be genes for amino acid hydroxylases, were discovered. The amino acid sequences encoded by the DNA sequences are shown in SEQ ID NOs:16 and 18.

From each DNA sequence, a DNA fragment of about 1 kbp was amplified by PCR. Each fragment obtained was introduced into pQE80L (manufactured by QIAGEN) according to the method described in Example 1. The plasmids obtained are hereinafter referred to as pVsPA4H and pBsPA4H, respectively.

Example 6

<Evaluation of Pipecolic Acid 4-Hydroxylase Activity>

Using the two kinds of plasmids pVsPA4H and pBsPA4H obtained in Example 5, transformation of E. coli (Escherichia coli) Rosetta 2 (DE3) (manufactured by Merck Millipore Corporation) was carried out according to an ordinary method. Each recombinant E. coli obtained was cultured with shaking at 30° C. using liquid LB medium supplemented with 50 mg/L ampicillin, 15 mg/L chloramphenicol, and 1 mmol/L IPTG for 20 hours, and the cultured bacterial cells were collected. Using cell-free extracts obtained from the collected cells, reaction was carried out at 20° C. at pH 6 for 21 hours in 50 mmol/L MES buffer supplemented with 15 mmol/L 2-oxoglutaric acid, 5 mmol/L ascorbic acid, 5 mmol/L tris(2-carboxyethyl)phosphine hydrochloride, 0.5 mmol/L FeSO$_4$.7H$_2$O, 3 mmol/L citric acid, and 10 mmol/L substrate compound (L-pipecolic acid).

The reaction liquids after the reaction were analyzed by the above-mentioned high-performance liquid chromatography (HPLC). As a result, a compound having the same molecular weight as trans-4-hydroxy-L-pipecolic acid was found in both reaction liquids.

The invention claimed is:

1. A pipecolic acid 4-hydroxylase protein having an activity to react with L-pipecolic acid in the presence of 2-oxoglutaric acid and iron(II) ions, to produce trans-4-hydroxy-L-pipecolic acid,
wherein the pipecolic acid 4-hydroxylase protein is selected from the group consisting of the following (A), (B-1), (B-2), (B-3), (B-4), (C-1), and (C-2), and the pipecolic acid 4-hydroxylase protein is a recombinant non-glycosylated protein:
(A) a polypeptide comprising the amino acid sequence of SEQ ID NO: 16 or 18;
(B-1) a polypeptide comprising the amino acid sequence of SEQ ID NO: 4, 6, 12, or 18 except that one to ten amino acids are deleted, substituted, and/or added, and having pipecolic acid 4-hydroxylase activity;
(B-2) a polypeptide comprising the amino acid sequence of SEQ ID NO: 2 except that one to five amino acids are deleted, substituted, and/or added, and having pipecolic acid 4-hydroxylase activity;
(B-3) a polypeptide comprising the amino acid sequence of SEQ ID NO: 8 or 10 except that one amino acid is deleted, substituted, and/or added, and having pipecolic acid 4-hydroxylase activity;
(B-4) a polypeptide comprising the amino acid sequence of SEQ ID NO: 16 except that one to five amino acids are deleted, substituted, and/or added, and having pipecolic acid 4-hydroxylase activity;
(C-1) a polypeptide comprising an amino acid sequence that is not less than 80% but not 100% identical to the amino acid sequence of SEQ ID NO: 4, 6, 12, or 18, and having pipecolic acid 4-hydroxylase activity; and (C-2) a polypeptide comprising an amino acid sequence that is not less than 95% but not 100% identical to the amino acid sequence of SEQ ID NO: 2, and having pipecolic acid 4-hydroxylase activity.

2. A microorganism having no glycosylation ability transformed with a DNA encoding a pipecolic acid 4-hydroxylase protein selected from the group consisting of the following (D), (E-1), (E-2), (E-3), and (E-4):
 (D) a DNA comprising the nucleotide sequence of SEQ ID NO: 15 or 17;
 (E-1) a DNA comprising the nucleotide sequence of SEQ ID NO: 3, 5, 11, or 17 except that one to three nucleotides are substituted, deleted, and/or added, and encoding a polypeptide having pipecolic acid 4-hydroxylase activity;
 (E-2) a DNA comprising the nucleotide sequence of SEQ ID NO: 1 except that one to three nucleotides are substituted, deleted, and/or added, and encoding a polypeptide having pipecolic acid 4-hydroxylase activity;
 (E-3) a DNA comprising the nucleotide sequence of SEQ ID NO: 7 or 9 except that one nucleotide is substituted, deleted, and/or added, and encoding a polypeptide having pipecolic acid 4-hydroxylase activity; and
 (E-4) a DNA comprising the nucleotide sequence of SEQ ID NO: 15 except that one to three nucleotides are substituted, deleted, and/or added, and encoding a polypeptide having pipecolic acid 4-hydroxylase activity.

3. The microorganism according to claim 2, which is selected from the group consisting of the genera *Escherichia, Bacillus, Pseudomonas*, and *Corynebacterium*.

* * * * *